(12) United States Patent
Kitano

(10) Patent No.: US 11,806,178 B2
(45) Date of Patent: Nov. 7, 2023

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM CORPORATION, Tokyo (JP)

(72) Inventor: Koichi Kitano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 99 days.

(21) Appl. No.: 17/337,433

(22) Filed: Jun. 3, 2021

(65) Prior Publication Data

US 2021/0383542 A1 Dec. 9, 2021

(30) Foreign Application Priority Data

Jun. 5, 2020 (JP) ................... 2020-098943

(51) Int. Cl.
*A61B 6/00* (2006.01)
*A61B 6/04* (2006.01)
(Continued)

(52) U.S. Cl.
CPC .......... *A61B 6/0492* (2013.01); *A61B 6/5211* (2013.01); *G01N 23/04* (2013.01);
(Continued)

(58) Field of Classification Search
CPC ......... G06T 7/0014; G06T 7/521; G06T 7/55; G06T 5/007; G06T 2207/10028;
(Continued)

(56) References Cited

U.S. PATENT DOCUMENTS

2006/0100509 A1* 5/2006 Wright ................. A61N 5/1049
600/414
2011/0317816 A1* 12/2011 Bechard ................. A61B 6/56
29/729
(Continued)

FOREIGN PATENT DOCUMENTS

CN 104053400 A * 9/2014 ............... A61B 6/06
ES 2614893 T3 * 6/2017 ............... A61B 6/00
(Continued)

OTHER PUBLICATIONS

Zhang et al., Convolutional Neural Network based Metal Artifact Reduction in X-ray Computed Tomography, 2018, arXiv: 1709.01581v2, pp. 1-13. (Year: 2018).*
(Continued)

*Primary Examiner* — John Villecco
*Assistant Examiner* — Kathleen M Broughton
(74) *Attorney, Agent, or Firm* — SOLARIS Intellectual Property Group, PLLC

(57) ABSTRACT

A CPU acquires a radiographic image obtained by imaging an imaging region where a patient is present, with a radioscopy apparatus using radiation emitted from a radiation source and applied to an irradiation field adjusted by a collimator. The CPU specifies a structure image that is included in the radiographic image and represents a structure of a specific shape having transmittance of radiation lower than the patient, based on the specific shape. The CPU executes image processing corresponding to the structure image on a patient image region imaged by a radioscopy (Continued)

apparatus in a case where an irradiation field excluding a position of the structure is set as the irradiation field, in a region in the radiographic image.

16 Claims, 16 Drawing Sheets

(51) Int. Cl.
*G06T 7/00* (2017.01)
*G06T 7/521* (2017.01)
*G06T 7/55* (2017.01)
*G06T 5/00* (2006.01)
*G01N 23/04* (2018.01)
*G06V 10/82* (2022.01)
*G06V 10/36* (2022.01)

(52) U.S. Cl.
CPC ............ *G06T 5/007* (2013.01); *G06T 7/0014* (2013.01); *G06T 7/521* (2017.01); *G06T 7/55* (2017.01); *G06V 10/36* (2022.01); *G06V 10/82* (2022.01); *G06T 2207/10028* (2013.01); *G06T 2207/10116* (2013.01); *G06T 2207/20081* (2013.01); *G06V 2201/03* (2022.01)

(58) Field of Classification Search
CPC . G06T 2207/10116; G06T 2207/20081; A61B 6/5211; A61B 6/5252; A61B 6/589; A61B 6/0492; G01N 23/04; G06V 10/40; G06V 10/36; G06V 10/82; G06V 2201/03; G06V 2201/031
See application file for complete search history.

(56) References Cited

U.S. PATENT DOCUMENTS

| | | | | |
|---|---|---|---|---|
| 2013/0136231 A1* | 5/2013 | Cox | .................... | G01V 5/0016 378/62 |
| 2015/0094516 A1* | 4/2015 | Taguchi | .................. | A61N 5/10 382/103 |
| 2015/0190107 A1* | 7/2015 | Kim | ........................ | A61B 6/032 600/407 |
| 2016/0078647 A1* | 3/2016 | Schildkraut | ............ | G06T 11/005 382/131 |
| 2017/0372454 A1* | 12/2017 | Takagi | .................... | G06T 5/002 |
| 2018/0137658 A1* | 5/2018 | Zhang | ........................ | G06T 7/13 |
| 2018/0264288 A1* | 9/2018 | Sakata | ................. | A61B 6/4014 |
| 2019/0046134 A1* | 2/2019 | Imamura | ................ | A61B 6/464 |
| 2019/0336033 A1* | 11/2019 | Takeshima | ............. | G06N 3/084 |

FOREIGN PATENT DOCUMENTS

| | | | |
|---|---|---|---|
| JP | 2000033082 A | * | 2/2000 |
| JP | 2006-198157 A | | 8/2006 |
| JP | 2018-153299 A | | 10/2018 |
| JP | 2019-033826 A | | 3/2019 |
| JP | 2020022689 A | * | 2/2020 |

OTHER PUBLICATIONS

Lin et al, DuDoNet: Dual Domain Network for CT Metal Artifact Reduction, 2019, arXiv:1907.00273v1, pp. 1-14. (Year: 2019).*
English language translation of the following: Office action dated Jun. 13, 2023 from the JPO in a Japanese patent application No. 2020-098943 corresponding to the instant patent application. This office action translation is submitted now in order to supplement the understanding of the cited references which are being disclosed in the instant Information Disclosure Statement.

* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2020-098943, filed on Jun. 5, 2020. The above application is hereby expressly incorporated by reference, in its entirety, into the present application.

BACKGROUND

1. Technical Field

The present disclosure relates to an image processing apparatus, a radiography system, an image processing method, and an image processing program.

2. Description of the Related Art

In general, in a case where a radiographic image of a subject is captured by a radiography apparatus, a structure other than the subject is present in an imaging region where the subject is present, and accordingly, the structure other than the subject may be imaged in the radiographic image. For example, JP2006-198157A describes a radiography apparatus that images a subject in a wheelchair. In the technique described in JP2006-198157A, the wheelchair is present as a structure other than the subject in an imaging region of the radiography apparatus, and accordingly, the wheelchair may be imaged in the radiographic image along with the subject.

SUMMARY

In general, image processing is executed on the radiographic image captured by the radiography apparatus, and the radiographic image after the image processing is provided to a physician, a technician, or the like. In a case where a structure other than the subject is imaged in the radiographic image, an image of the structure may affect the image processing. In particular, in a case where the structure has transmittance of radiation lower than the subject, the image quality of the radiographic image may be degraded as affected by a structure image representing the structure.

For example, in the technique described in JP2006-198157A, the wheelchair generally has transmittance of radiation lower than the subject. For this reason, in the technique described in JP2006-198157A, the image quality of the radiographic image may be degraded as affected by an image representing the wheelchair in the radiographic image.

The present disclosure has been accomplished in view of the above-described situation, and an object of the present disclosure is to provide an image processing apparatus, a radiography system, an image processing method, and an image processing program capable of improving image quality of a radiographic image.

To achieve the above-described object, a first aspect of the present disclosure provides an image processing apparatus comprising at least one processor. The processor is configured to acquire a radiographic image obtained by imaging an imaging region where a subject is present, with a radiography apparatus using radiation emitted from a radiation source and applied to an irradiation field adjusted by a collimator, specify a structure image that is included in the radiographic image and represents a structure of a specific shape having transmittance of radiation lower than the subject, based on the specific shape, and execute image processing corresponding to the structure image on a region that is imaged by the radiography apparatus in a case where an irradiation field excluding a position of the structure is set as the irradiation field, in a region in the radiographic image.

According to a second aspect of the present disclosure, in the image processing apparatus of the first aspect, the processor is configured to acquire a distance to an imaging target in the imaging region, and specify the structure image based on the distance and the specific shape.

According to a third aspect of the present disclosure, in the image processing apparatus of the second aspect, the processor is configured to acquire a distance image captured by a distance image capturing apparatus that captures a distance image representing a distance to the imaging target, and acquire the distance based on the distance image.

According to a fourth aspect of the present disclosure, in the image processing apparatus of the third aspect, the distance image capturing apparatus captures the distance image using a time-of-flight (TOF) system.

According to a fifth aspect of the present disclosure, in the image processing apparatus of the third aspect, the processor is configured to detect a structure distance image corresponding to the specific shape from the distance image based on the distance, and specify, as the structure image, an image corresponding to the structure distance image from the radiographic image.

According to a sixth aspect of the present disclosure, in the image processing apparatus of the fifth aspect, the processor is configured to detect the structure distance image based on a learned model learned in advance using a plurality of the distance images with the structure in the imaging region as the imaging target.

According to a seventh aspect of the present disclosure, in the image processing apparatus of the third aspect, the processor is configured to specify the structure image based on a learned model learned in advance using a plurality of combinations of the radiographic image and the distance image with the structure in the imaging region as the imaging target.

According to an eighth aspect of the present disclosure, in the image processing apparatus of the second aspect, the processor is configured to acquire a visible light image obtained by imaging the imaging region with a visible light image capturing apparatus, and specify the structure image included in the radiographic image based on a shape detected from the visible light image and the distance.

According to a ninth aspect of the present disclosure, in the image processing apparatus of the first aspect, the processor is configured to acquire a visible light image obtained by imaging the imaging region with a visible light image capturing apparatus, detect a structure visible light image corresponding to the specific shape from the visible light image, and specify, as the structure image, an image corresponding to the structure visible light image from the radiographic image.

According to a tenth aspect of the present disclosure, in the image processing apparatus of the first aspect, the structure consists of metal.

According to an eleventh aspect of the present disclosure, in the image processing apparatus of the first aspect, the structure is a wheelchair.

According to a twelfth aspect of the present disclosure, in the image processing apparatus of the first aspect, the structure is a stretcher.

According to a thirteenth aspect of the present disclosure, in the image processing apparatus of the first aspect, the processor is configured to execute image processing with a degree derived from a region in the radiographic image other than the structure image.

According to a fourteenth aspect of the present disclosure, in the image processing apparatus of the first aspect, the processor is configured to execute the image processing on a region other than the structure image in the radiographic image.

According to a fifteenth aspect of the present disclosure, in the image processing apparatus of the first aspect, the image processing is contrast enhancement processing.

To achieve the above-described object, a sixteenth aspect of the present disclosure provides a radiography system comprising a radiography apparatus that captures a radiographic image of a subject, and the image processing apparatus of the present disclosure.

To achieve the above-described object, a seventeenth aspect of the present disclosure provides an image processing method in which a computer executes processing of acquiring a radiographic image obtained by imaging an imaging region where a subject is present, with a radiography apparatus using radiation emitted from a radiation source and applied to an irradiation field adjusted by a collimator, specifying a structure image that is included in the radiographic image and represents a structure of a specific shape having transmittance of radiation lower than the subject, based on the specific shape, and executing image processing corresponding to the structure image on a region that is imaged by the radiography apparatus in a case where an irradiation field excluding a position of the structure is set as the irradiation field, in a region in the radiographic image.

To achieve the above-described object, an eighteenth aspect of the present disclosure provides a non-transitory computer-readable storage medium storing an image processing program causing a computer to execute processing of acquiring a radiographic image obtained by imaging an imaging region where a subject is present, with a radiography apparatus using radiation emitted from a radiation source and applied to an irradiation field adjusted by a collimator, specifying a structure image that is included in the radiographic image and represents a structure of a specific shape having transmittance of radiation lower than the subject, based on the specific shape, and executing image processing corresponding to the structure image on a region that is imaged by the radiography apparatus in a case where an irradiation field excluding a position of the structure is set as the irradiation field, in a region in the radiographic image.

According to the present disclosure, it is possible to improve image quality of a radiographic image.

BRIEF DESCRIPTION OF THE DRAWINGS

Exemplary embodiments according to the technique of the present disclosure will be described in detail based on the following figures, wherein.

DETAILED DESCRIPTION

Figure 1:
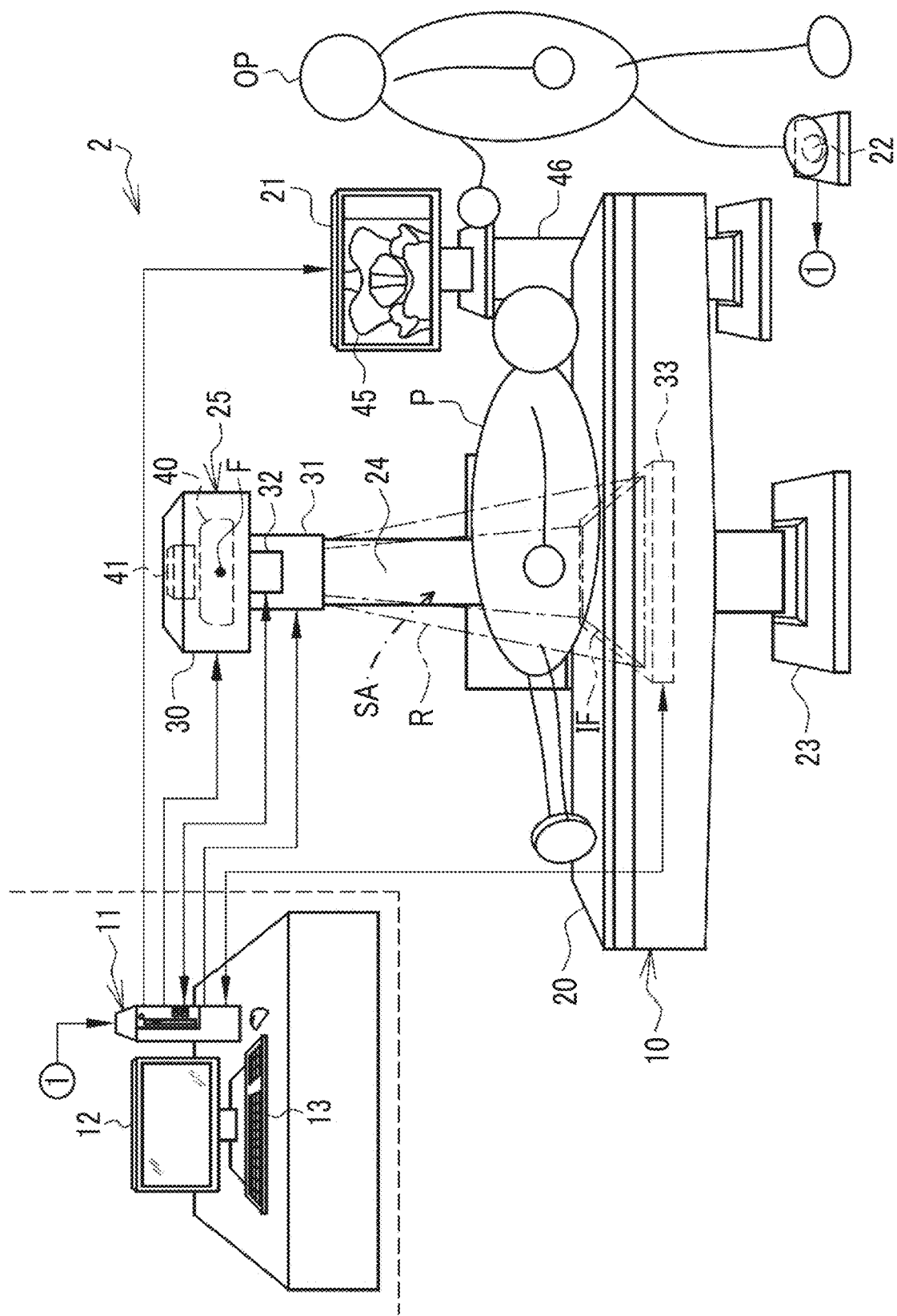
FIG. 1 is a diagram showing an example of a radioscopy system.

Hereinafter, embodiments of the present disclosure will be described in detail referring to the drawings. Each embodiment is not intended to limit the present disclosure.

First Embodiment

First, an example of the overall configuration in a radioscopy system of the embodiment will be described. As shown in FIG. 1, a radioscopy system 2 of the embodiment comprises a radioscopy apparatus 10 and a console 11. The radioscopy apparatus 10 is provided in, for example, an operation room of a medical facility. The operation room is a room where an operator OP, such as a radiographer or a physician, performs an operation, such as a gastric barium test, cystography, or orthopedic reduction, to a patient P. The radioscopy apparatus 10 performs radioscopy to the patient P under operation. The radioscopy apparatus 10 of the embodiment is an example of a "radiography apparatus" of the present disclosure, and the patient P of the embodiment is an example of a "subject" of the present disclosure.

The console 11 is an example of an "image processing apparatus" of the present disclosure, and is provided, for example, in a control room next to the operation room. The console 11 controls the operation of each unit of the radioscopy apparatus 10. The console 11 is, for example, a desktop personal computer, and has a display 12 and an input device 13, such as a keyboard or a mouse. The display 12 displays an imaging order or the like from a radiology information system (RIS). The input device 13 is operated by the operator OP in designating an imaging menu corresponding to the imaging order, or the like.

The radioscopy apparatus 10 has an imaging table 20, an operator monitor 21, a foot switch 22, and the like. The imaging table 20 is supported on a floor surface of the operation room by a stand 23. A radiation generation unit 25 is attached to the imaging table 20 through a post 24. The radiation generation unit 25 includes a radiation source 30, a collimator 31, and a distance measurement camera 32. A radiation detector 33 is incorporated in the imaging table 20.

The radiation source 30 has a radiation tube 40. The radiation tube 40 emits radiation R, such as X-rays or y-rays, and irradiates the patient P lying on the imaging table 20 with the radiation R, for example. The radiation tube 40 is provided with a filament, a target, a grid electrode, and the like (all are not shown). A voltage is applied between the filament as a cathode and the target as an anode from a voltage generator 41. The voltage that is applied between the filament and the target is referred to as a tube voltage. The filament discharges thermoelectrons according to the applied tube voltage toward the target. The target radiates the radiation R with collision of the thermoelectrons from the filament. The grid electrode is disposed between the filament and the target. The grid electrode changes a flow rate of the thermoelectrons from the filament toward the target depending on the voltage applied from the voltage generator 41. The flow rate of the thermoelectrons from the filament toward the target is referred to as a tube current.

The collimator 31 and the distance measurement camera 32 are attached to a lower portion of the radiation source 30. The collimator 31 adjusts an irradiation field IF of the radiation R generated from the radiation tube 40. In other words, the collimator 31 adjusts an imaging region SA of a radiographic image 45 by the radioscopy apparatus 10. As an example, in the embodiment, the irradiation field IF has a rectangular shape. For this reason, the irradiation of the radiation R emitted from a focus F of the radiation source 30 is performed to a quadrangular pyramid-shaped region with the focus F as an apex and the irradiation field IF as a bottom surface. The quadrangular pyramid-shaped region to which the irradiation of the radiation R is performed from the radiation tube 40 to the radiation detector 33 is the imaging region SA of the radiographic image 45 by the radioscopy apparatus 10. The radioscopy apparatus 10 captures a radiographic image 45 of an imaging target in the imaging region SA. In the embodiment, the imaging target of the radioscopy apparatus 10 refers to an object in the imaging region SA in addition to the patient P, and refers to an object in the radiographic image 45 captured by the radioscopy apparatus 10.

For example, the collimator 31 has a configuration in which four shield plates (not shown) formed of lead or the like shielding the radiation R are disposed on respective sides of a quadrangle, and an emission opening of the quadrangle transmitting the radiation R is formed in a center portion. The collimator 31 changes the positions of the respective shield plates to change an opening degree of the emission opening, and accordingly, adjusts the imaging region SA and the irradiation field IF.

The distance measurement camera 32 is a camera that captures a distance image representing a distance to the imaging target using a time-of-flight (TOF) system. The distance measurement camera 32 is an example of a "distance image capturing apparatus" of the present disclosure. Specifically, the distance measurement camera 32 measures a distance between the distance measurement camera 32 and the imaging target, and specifically, a distance between the distance measurement camera 32 and a surface of the imaging target based on a time from when the imaging target is irradiated with light, such as infrared rays, until reflected light is received or a change in phase between emitted light and received light. An imaging range of the distance measurement camera 32 of the embodiment includes the whole of the imaging region SA of the radioscopy apparatus 10. Accordingly, the distance measurement camera 32 of the embodiment measures the distance between the distance measurement camera 32 and the imaging target of the radioscopy apparatus 10. The measurement of the distance by the distance measurement camera 32 is not performed to an imaging target behind (under) another imaging target as viewed from the distance measurement camera 32 among the imaging targets in the imaging region SA.

The distance image captured by the distance measurement camera 32 has distance information representing the distance between the distance measurement camera 32 and the imaging target for each pixel. The distance image captured by the distance measurement camera 32 of the embodiment has information representing the distance between the distance measurement camera 32 and the imaging target as a pixel value of each pixel. The distance image refers to an image from which the distance to the imaging target can be derived.

In the embodiment, the distance image captured by the distance measurement camera 32 and the radiographic image 45 captured by the radioscopy apparatus 10 are registered in advance. Specifically, correspondence relationship information indicating an image represented by a pixel in the distance image to which an image represented by a pixel of the radiographic image 45 corresponds is obtained in advance.

In a case where the positions of the distance measurement camera 32 and the radiation source 30 are identical, more accurately, in a case where positions of an imaging element (not shown) of the distance measurement camera 32 and the focus F of the radiation tube 40 are considered to be identical, the distance measurement camera 32 measures the distance between the radiation source 30 and an imaging target of the distance measurement camera 32. In a case where the positions of the distance measurement camera 32 and the radiation source 30 are different, a result obtained by adding a distance between the focus F and the imaging element of the distance measurement camera 32 measured in advance to the distance measured with the distance measurement camera 32 may be set as the distance between the radiation source 30 and the imaging target.

The radiation detector 33 has a configuration in which a plurality of pixels that are sensitive to the radiation R or visible light converted from the radiation R by a scintillator to generate signal charge are arranged. Such a radiation detector 33 is referred to as a flat panel detector (FPD). The radiation detector 33 detects the radiation R emitted from the radiation tube 40 and transmitted through the patient P, and outputs a radiographic image 45. The radiation detector 33 outputs the radiographic image 45 to the console 11. More specifically, the radiation detector 33 outputs image data representing the radiographic image 45 to the console 11.

The radiographic images 45 captured as video are also referred to as radioscopic images.

The operator monitor 21 is supported on the floor surface of the operation room by a stand 46. The radiographic images 45 output from the radiation detector 33 and subjected to various kinds of image processing described below in detail with the console 11 are displayed on the operator monitor 21 in a form of video in real time.

The foot switch 22 is a switch for the operator OP giving an instruction to start and end radioscopy while being seated in the operation room. In a case where the operator OP depresses the foot switch 22 with a foot, radioscopy is started. Then, while the operator OP is depressing the foot switch 22 with the foot, radioscopy is continued. In a case where the foot switch 22 is depressed with the foot of the operator OP, the tube voltage is applied from the voltage generator 41, and the radiation R is generated from the radiation tube 40. In a case where the operator OP releases the foot from the foot switch 22, and the depression of the foot switch 22 is released, radioscopy ends.

Figure 2:
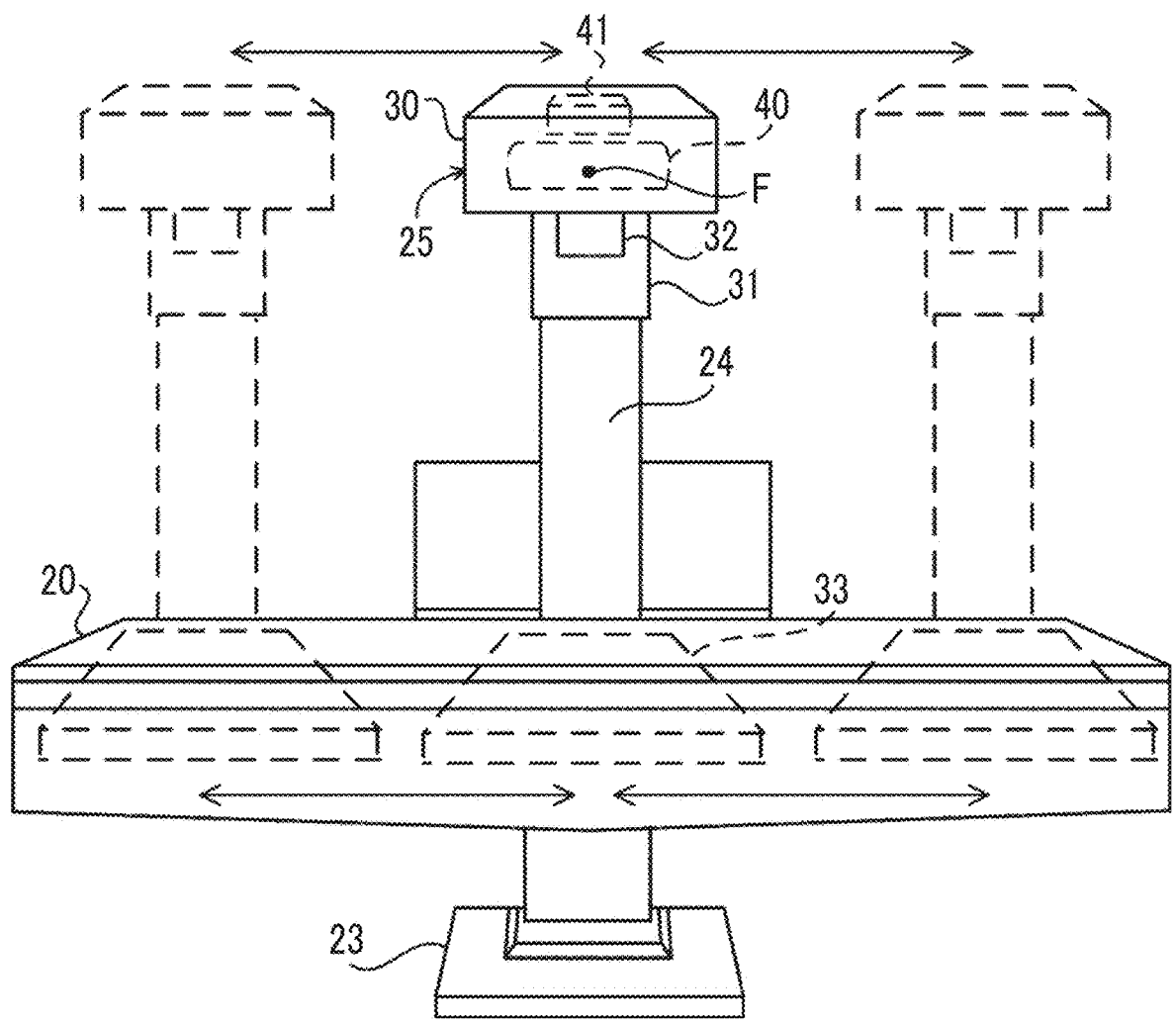
FIG. 2 is a diagram showing a manner in which a radiation generation unit and a radiation detector reciprocate along a longitudinal direction of an imaging table.

As shown in FIG. 2, not only the post 24 but also the radiation generation unit 25 can reciprocate along a longitudinal direction of the imaging table 20 by a movement mechanism (not shown), such as a motor. The radiation detector 33 can also reciprocate along the longitudinal direction of the imaging table 20 in conjunction with the movement of the radiation generation unit 25. The radiation detector 33 is moved to a facing position where the center thereof coincides with the focus F of the radiation tube 40. The imaging table 20 is provided with a control panel (not shown) for inputting an instruction to move the radiation generation unit 25 and the radiation detector 33. The operator OP inputs an instruction through the control panel and moves the radiation generation unit 25 and the radiation detector 33 to desired positions. The radiation generation unit 25 and the radiation detector 33 can be controlled by remote control by a control console (not shown) from the control room.

Figure 3:
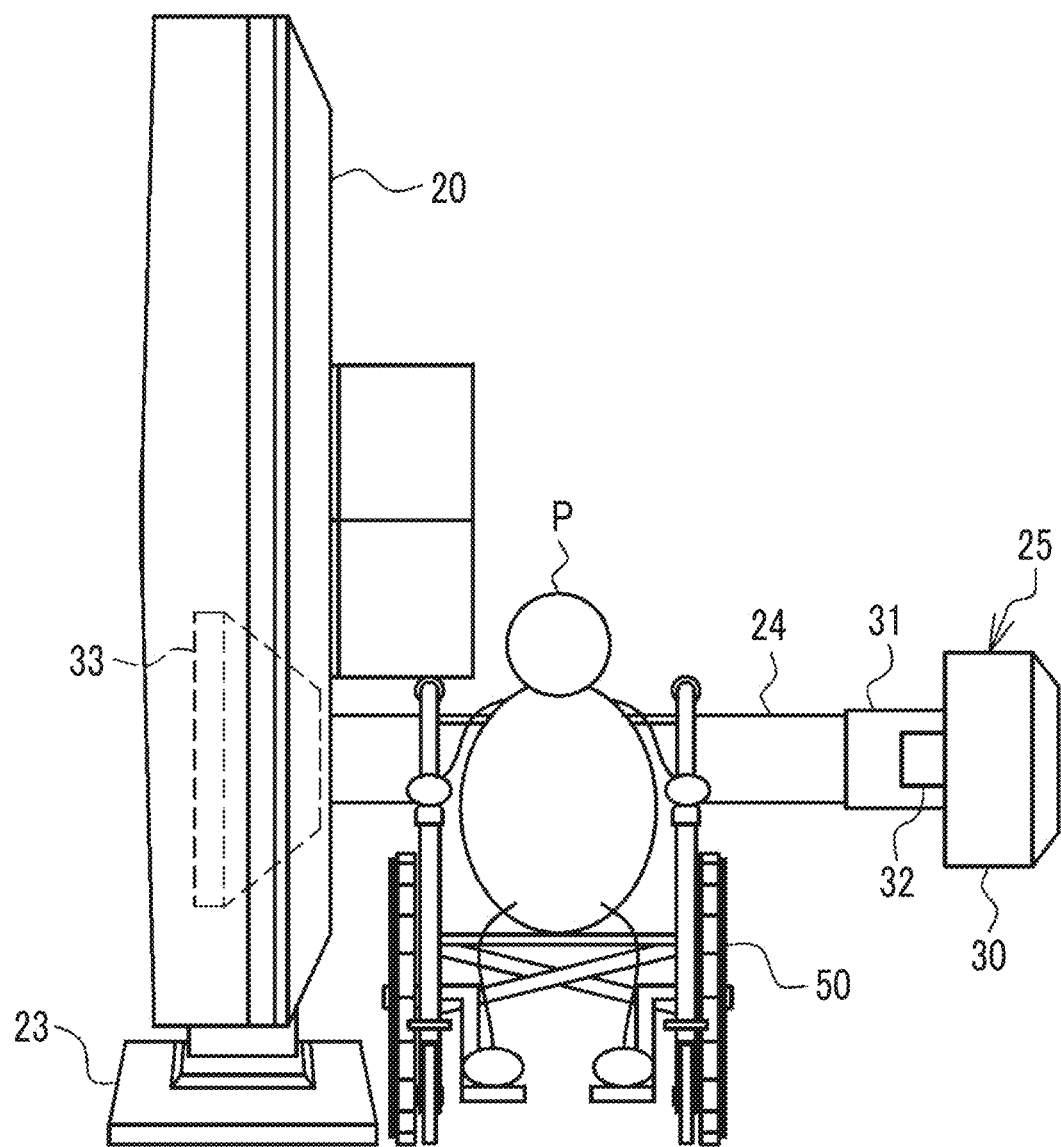
FIG. 3 is a diagram showing a manner in which radioscopy is performed on a patient in a wheelchair with an imaging table and a post in an upright state.
Figure 4A:
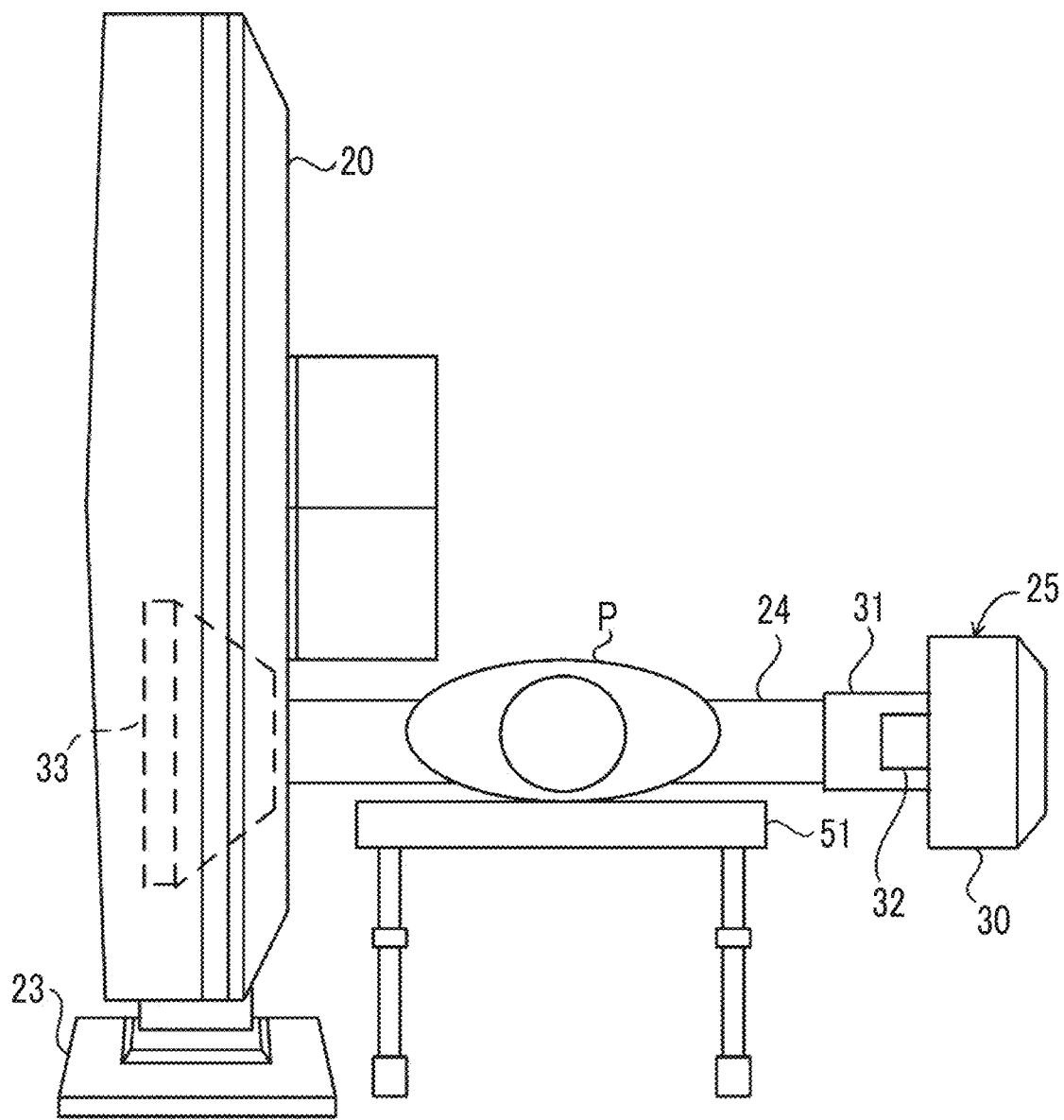
FIG. 4A is a diagram showing an example of a manner in which radioscopy is performed on a patient on a stretcher with the imaging table and the post in the upright state.
Figure 4B:
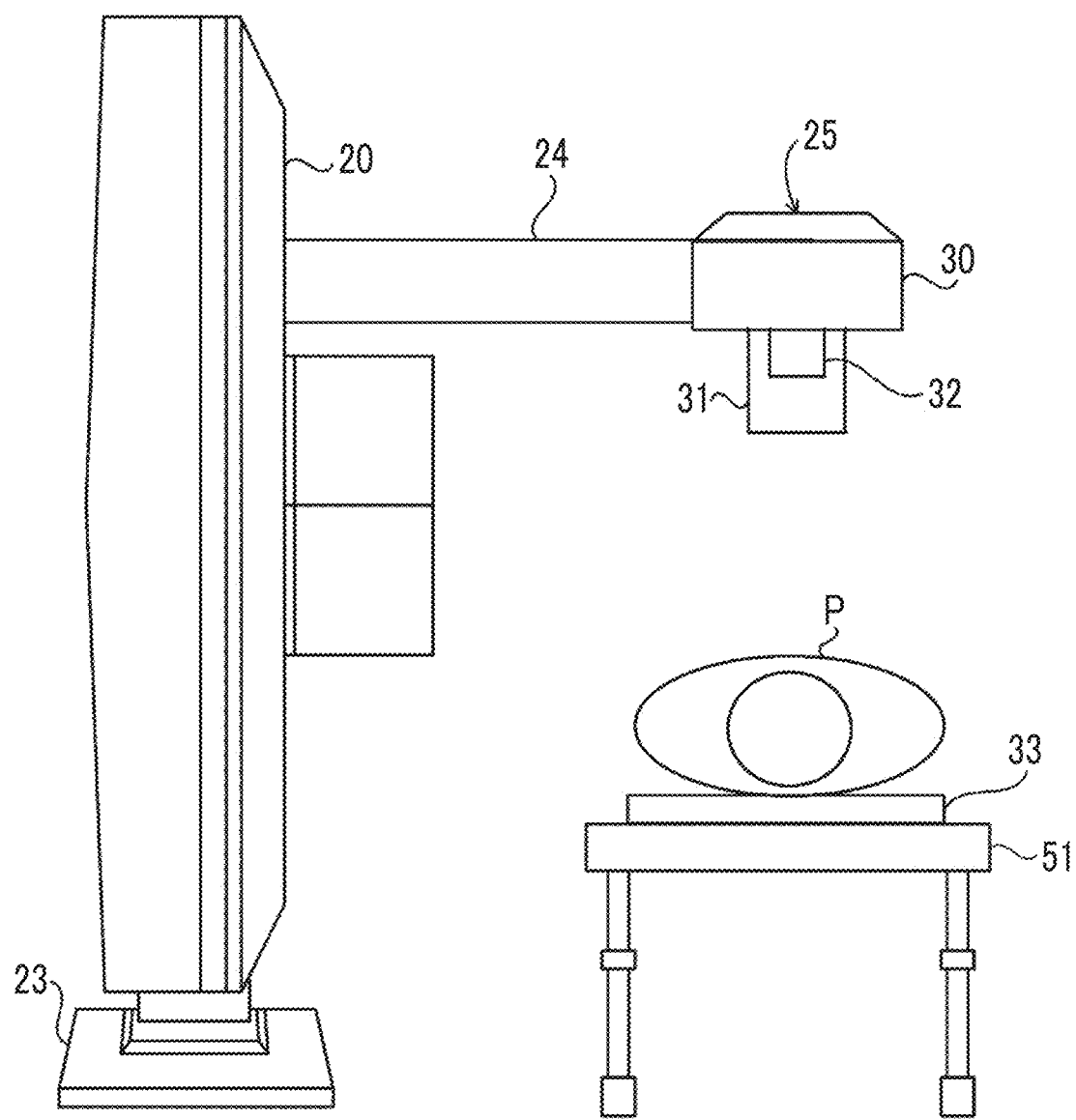
FIG. 4B is a diagram showing another example of a manner in which radioscopy is performed on the patient on the stretcher with the imaging table and the post in the upright state.

The imaging table 20 and the post 24 can rotate between a decubitus state shown in FIGS. 1 and 2 and an upright state shown in FIGS. 3, 4A, and 4B by a rotation mechanism (not shown), such as a motor. The decubitus state is a state in which the surface of the imaging table 20 is parallel to the floor surface and the post 24 is perpendicular to the floor surface. On the contrary, the upright state is a state in which the surface of the imaging table 20 is perpendicular to the floor surface, and the post 24 is parallel to the floor surface. In the upright state, not only radioscopy on the patient P in an upright posture, but also radioscopy on the patient P in a wheelchair 50 as shown in FIG. 3 can be performed. In the upright state, as shown in FIGS. 4A and 4B, radioscopy can be performed on the patient P on a stretcher 51. In a case shown in FIG. 4A, similarly to the state shown in FIG. 3, imaging of the radiographic image 45 by the radioscopy apparatus 10 is performed. On the other hand, in a case shown in FIG. 4B, unlike the state shown in FIG. 4A, the radiation detector 33 is detached from the imaging table 20 and is set between the patient P and the stretcher 51.

Figure 5:
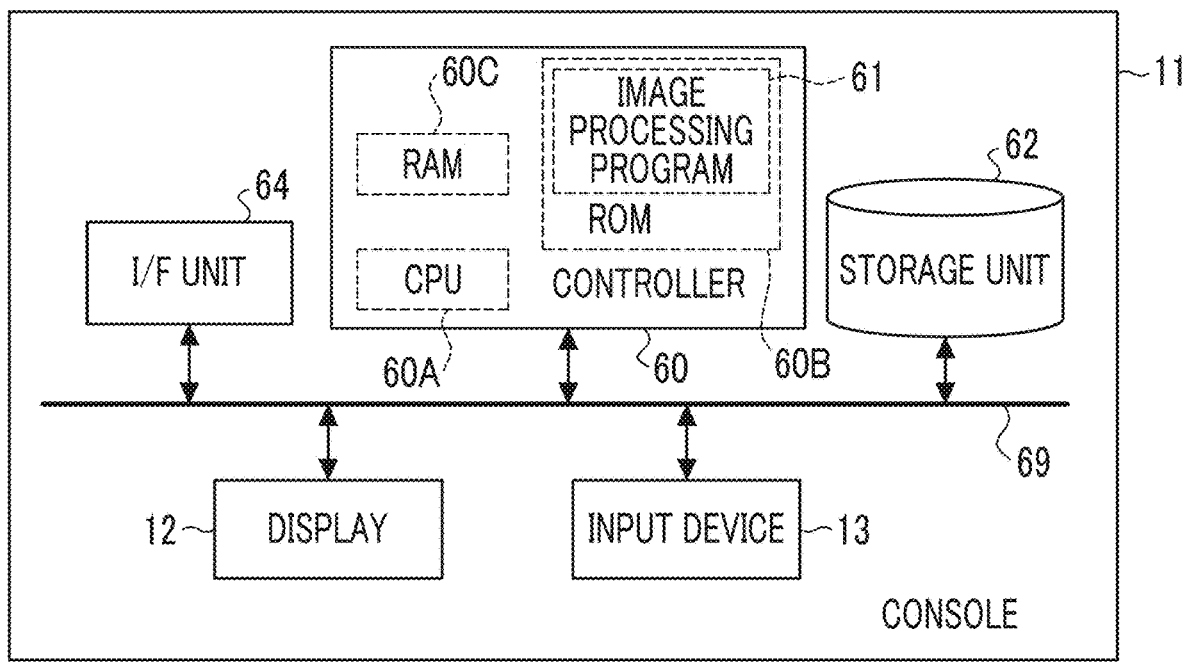
FIG. 5 is a block diagram showing an example of the hardware configuration of a console of a first embodiment.

The console 11 of the embodiment shown in FIG. 5 comprises the display 12 and the input device 13 described above, a controller 60, a storage unit 62, and an interface (I/F) unit 64. The display 12, the input device 13, the controller 60, the storage unit 62, and the I/F unit 64 are connected to transfer various kinds of information through a bus 69, such as a system bus or a control bus.

The controller 60 of the embodiment controls the operation of the whole of the console 11. The controller 60 comprises a central processing unit (CPU) 60A, a read only memory (ROM) 60B, and a random access memory (RAM) 60C. Various programs including an image processing program 61 to be executed with the CPU 60A, and the like are stored in advance in the ROM 60B. The RAM 60C temporarily stores various kinds of data. The CPU 60A of the embodiment is an example of a processor of the present disclosure. The image processing program 61 of the embodiment is an example of an "image processing program" of the present disclosure.

Image data of the radiographic image 45 captured by the radioscopy apparatus 10 and various other kinds of information (details will be described below) are stored in the storage unit 62. As a specific example of the storage unit 62, a hard disk drive (HDD), a solid state drive (SSD), or the like is exemplified.

The I/F unit 64 performs communication of various kinds of information between the radioscopy apparatus 10 and the radiology information system (RIS) (not shown) by wireless communication or wired communication. In the radioscopy system 2 of the embodiment, the console 11 receives image data of the radiographic image 45 captured by the radioscopy apparatus 10 from the radiation detector 33 of the radioscopy apparatus 10 by wireless communication or wired communication through the I/F unit 64.

Figure 6:
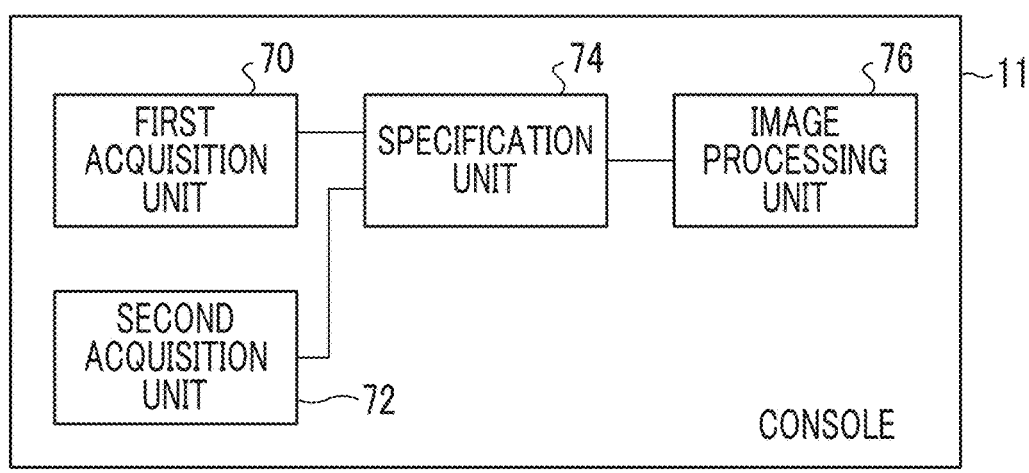
FIG. 6 is a functional block diagram showing an example of the functional configuration of the console of the first embodiment.

FIG. 6 is a functional block diagram of an example of the functional configuration of the console 11 of the embodiment. As shown in FIG. 6, the console 11 comprises a first acquisition unit 70, a second acquisition unit 72, a specification unit 74, and an image processing unit 76. As an example, in the console 11 of the embodiment, the CPU 60A of the controller 60 executes the image processing program 61 stored in the ROM 60B, whereby the CPU 60A functions as the first acquisition unit 70, the second acquisition unit 72, the specification unit 74, and the image processing unit 76.

The first acquisition unit 70 has a function of acquiring the radiographic image 45 captured by the radioscopy apparatus 10. As an example, the first acquisition unit 70 of the embodiment acquires image data representing the radiographic image 45 captured by the radioscopy apparatus 10 from the radiation detector 33 through the I/F unit 64. Image data representing the radiographic image 45 acquired by the first acquisition unit 70 is output to the specification unit 74.

The second acquisition unit 72 has a function of acquiring the distance image captured by the distance measurement camera 32. As an example, the second acquisition unit 72 of the embodiment acquires image data representing the distance image captured by the distance measurement camera 32 from the distance measurement camera 32 through the I/F unit 64. Image data representing the distance image acquired by the second acquisition unit 72 is output to the specification unit 74.

The specification unit 74 specifies a structure image that is included in the radiographic image 45 and represents a structure of a specific shape having transmittance of the radiation R lower than the patient P, based on the specific shape of the structure. As a material having transmittance of the radiation R lower than the patient P, metal or the like is exemplified.

Figure 7:
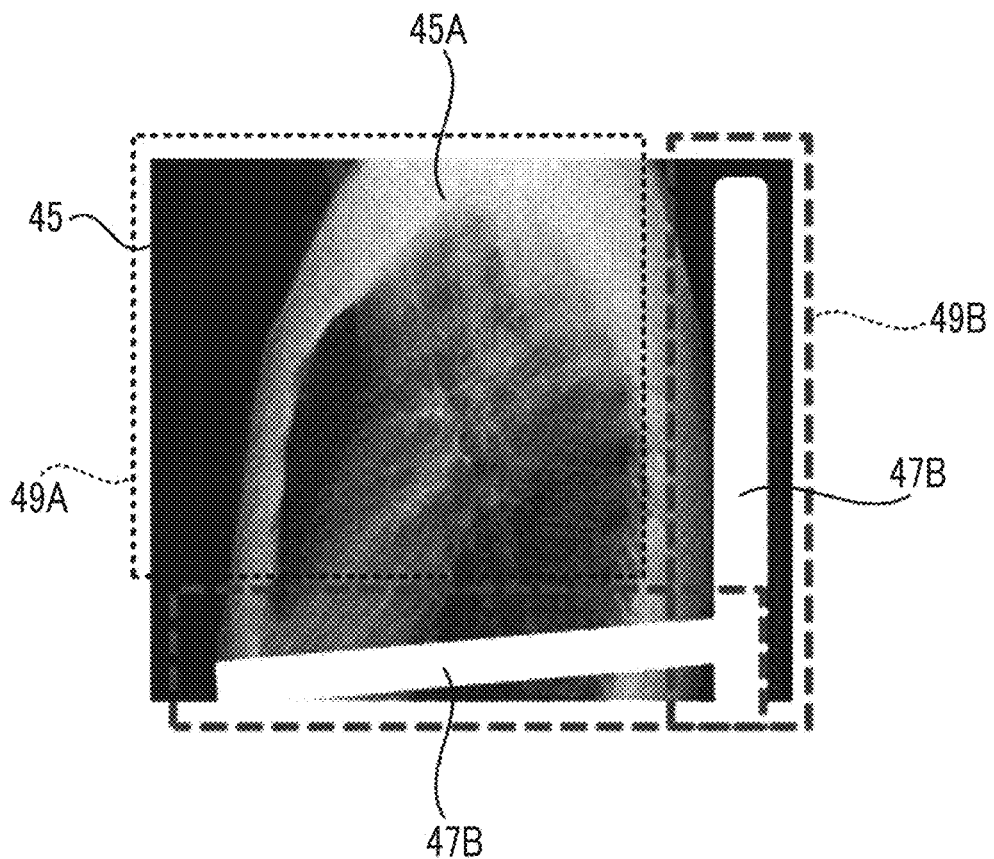
FIG. 7 is a diagram showing an example of a radiographic image in which a patient image and a structure image are included.

FIG. 7 shows an example of a radiographic image 45 in a case where the wheelchair 50 is imaged as the structure of the specific shape along with the patient P. In the radiographic image 45 shown in FIG. 7, a patient image 47A and a structure image 47B are included.

The wheelchair 50 of the embodiment is formed of a material having transmittance of the radiation R lower than the patient P, for example, metal. For this reason, as shown in FIG. 7, the structure image 47B is an image (hereinafter, referred to as a "low density image") having a density lower than the patient image 47A. In a case where image processing is executed to the entire radiographic image 45 in a state in which the low density image is present in this way, the image of the patient image 47A may not be brought into an appropriate state (image quality) as affected by the low density image. For example, in a case where dynamic range compression processing that is processing of enhancing contrast is executed as image processing, the patient image 47A appears low in contrast as affected by the low density image. As an area of the low density image is greater or the density of the low density image is lower, the contrast of the patient image 47A is lower.

In this way, examples of a material that becomes a low density image affecting the image quality of the radiographic image 45, and more specifically, the image quality of the patient image 47A include metal as described above. Examples of an object that is formed of metal or the like and is imaged in the radiographic image 45 along with the patient P include the wheelchair 50 (see FIG. 3) and the stretcher 51 (see FIG. 4A). The wheelchair 50 or the stretcher 51 is often disposed in a predetermined state in imaging of the radiographic image 45. For this reason, in a case where the wheelchair 50 or the stretcher 51 is imaged in the radiographic image 45 along with the patient P, the shape of the structure image 47B by the wheelchair 50 or the stretcher 51 often becomes a specific shape.

Accordingly, the specification unit 74 of the embodiment specifies the structure image 47B included in the radiographic image 45. The specification unit 74 outputs, to the image processing unit 76, information representing a patient image region 49A (see FIG. 7) where the patient image 47A is included, excluding a structure image region 49B (see FIG. 7) where the structure image 47B is included.

The image processing unit 76 has a function of executing image processing corresponding to the structure image 47B on the radiographic image. The image processing that is executed by the image processing unit 76 of the embodiment includes at least dynamic range compression processing of enhancing contrast. A specific method of the dynamic range compression processing is not particularly limited. As the dynamic range compression processing, for example, a method described in JP1998-075364A (JP-H10-075364A) may be used. In the method described in JP1998-075364A (JP-H10-075364A), a plurality of band-limited images are created from a radiographic image 45, and an image regarding a low-frequency component of the radiographic image 45 is obtained based on the band-limited images. Then, an output value obtained by converting the obtained image regarding the low-frequency component by a compression table is added to the radiographic image 45, and dynamic range compression processing is executed. With the execution of the dynamic range compression processing, it is possible to obtain the radiographic image 45 with contrast enhanced, for example, with contrast set in advance.

Although examples of other kinds of image processing to be executed by the image processing unit 76 include offset correction processing, sensitivity correction processing, and defective pixel correction processing, the present disclosure is not limited thereto.

The image processing unit 76 of the embodiment executes the above-described image processing as the image processing corresponding to the structure image 47B on a region other than the structure image region 49B including the structure image 47B in the radiographic image 45. In the case shown in FIG. 7, for example, the image processing by the image processing unit 76 is executed on the patient image region 49A including the patient image 47A in the radiographic image 45 without taking into consideration an image characteristic and an image density of the structure image 47B. For example, the image processing unit 76 executes the dynamic range compression processing on the patient image region 49A with a degree derived corresponding to an image characteristic and an image density of the patient image region 49A. For example, a form may be made in which the image processing by the image processing unit 76 is executed on the patient image region 49A, while the image processing by the image processing unit 76 is not executed on the structure image region 49B.

In the embodiment, as the region other than the structure image 47B, a region corresponding to the radiographic image 45 captured by the radioscopy apparatus 10 in a case where the irradiation field IF excluding the position of the structure of the specific shape is set as the irradiation field IF to be adjusted by the collimator 31 of the radioscopy apparatus 10, in a region in the radiographic image 45 is employed as the patient image region 49A. In other words, a region corresponding to the radiographic image 45 in a case where the imaging region SA including the patient P and excluding the structure having the specific shape from the imaging target is imaged is employed as the patient image region 49A.

Unlike the embodiment, as the image processing corresponding to the structure image 47B, for example, the above-described dynamic range compression processing or the like may be executed with a degree corresponding to the size of the structure image 47B that is a ratio of the structure image 47B to the entire radiographic image 45 or the patient image 47A, the density of the structure image 47B, or the like. A form may be made in which image processing other than the dynamic range compression processing is executed as the image processing to the structure image 47B.

Next, the operation of the console 11 of the embodiment will be described referring to the drawings.

Figure 8:
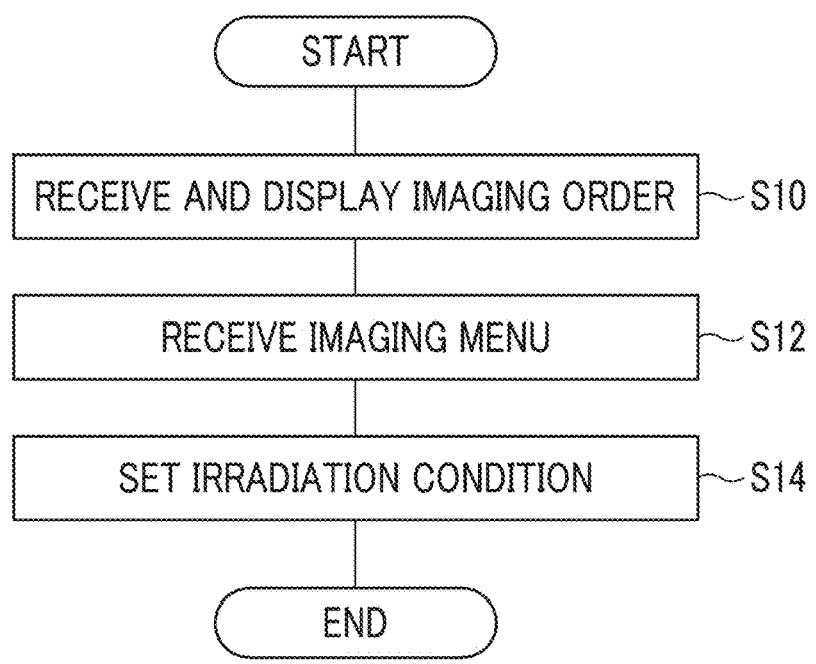
FIG. 8 is a flowchart showing an example of a procedure for setting irradiation conditions.

As shown in FIG. 8, prior to radioscopy, the console 11 receives the imaging order from the RIS and displays the imaging order on the display 12 (Step S10). In the imaging order, patient identification data (ID) for identifying the patient P, an instruction of an operation by a physician of a treatment department who issues the imaging order, and the like are registered. The operator OP confirms the content of the imaging order through the display 12.

The console 11 displays a plurality of kinds of imaging menus prepared in advance on the display 12 in an alternatively selectable form. The operator OP selects one imaging menu coinciding with the content of the imaging order through the input device 13. In the embodiment, an imaging menu is determined in advance for each part, such as chest or abdomen, and the operator OP selects the imaging menu by selecting an imaging part. With this, the console 11 receives an instruction of the imaging menu (Step S12).

The console 11 sets irradiation conditions corresponding to the instructed imaging menu (Step S14). In the embodiment, the irradiation conditions are associated with each imaging menu. As the irradiation conditions, the tube voltage, the tube current, an irradiation time, and a range of the irradiation field IF are included. As an example, in the embodiment, information in which the imaging menu and the irradiation conditions are associated is stored in advance in the storage unit 62. For this reason, the console 11 outputs information representing the tube voltage, the tube current, the irradiation time, and the range of the irradiation field IF as the irradiation conditions to the radioscopy apparatus 10.

In the radioscopy apparatus 10, the tube voltage and the tube current are set in the radiation source 30. The collimator 31 of the radioscopy apparatus 10 adjusts the irradiation field IF by the above-described shield plates (not shown). The irradiation conditions have content where the irradiation of the radiation R is performed with an extremely low dose compared to a case where general radiography is performed.

After selecting the imaging menu, the operator OP performs positioning and the like of the radiation source 30, the radiation detector 33, and the patient P, and depresses the foot switch 22 with the foot to start radioscopy.

Figure 9:
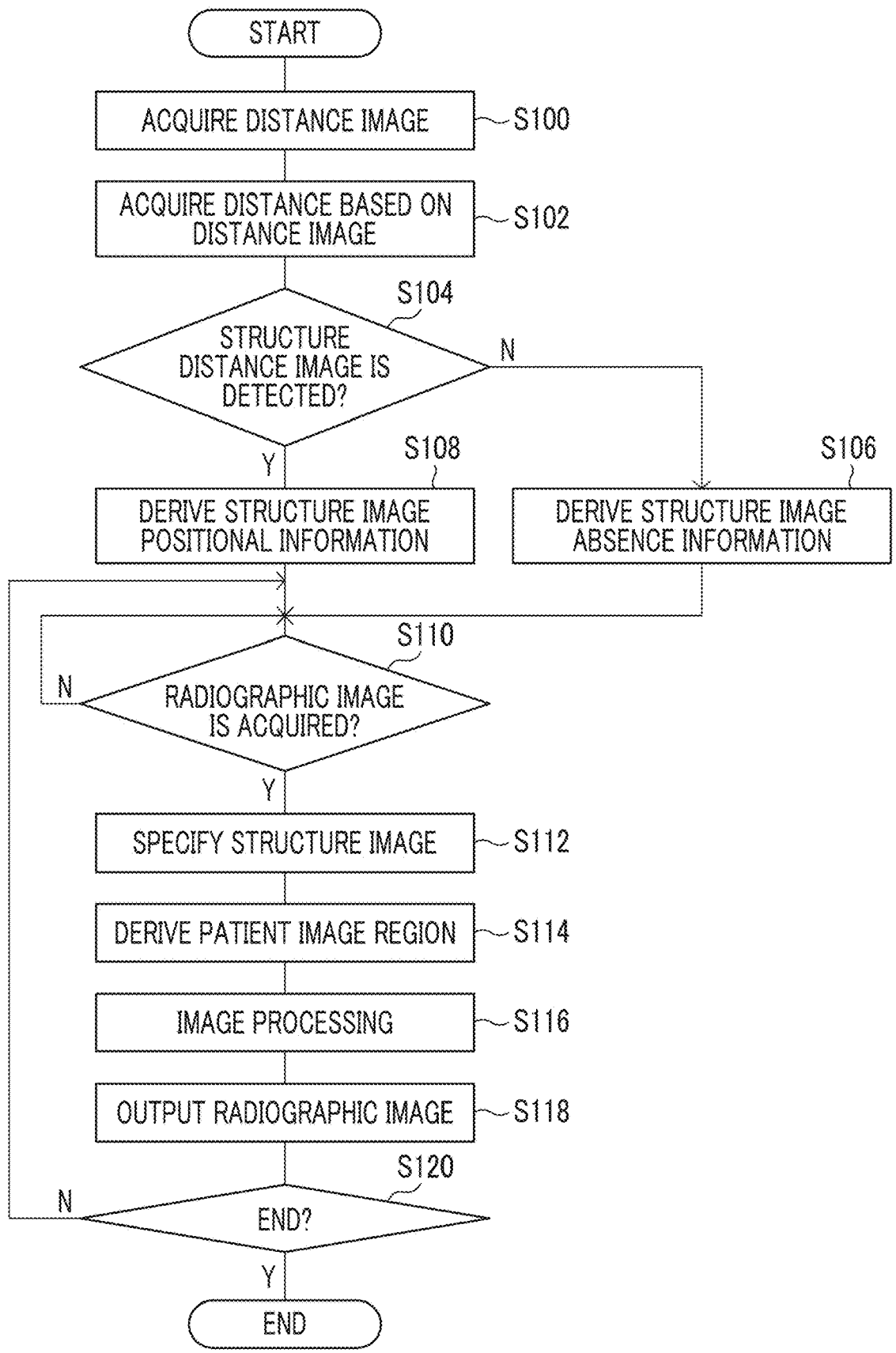
FIG. 9 is a flowchart showing an example of a flow of image processing in the console of the first embodiment.

In the console 11 of the embodiment, in a case where the imaging order is received (FIG. 8, S10), image processing shown in FIG. 9 is executed. A timing at which the image processing shown in FIG. 9 is executed is not limited to the timing in the embodiment, and may be, for example, a timing at which the irradiation conditions are sets (FIG. 8, S14) or a timing immediately after the irradiation conditions are set. The timing at which the image processing shown in FIG. 9 may be any timing during imaging of the radiographic image 45. In the console 11 of the embodiment, the CPU 60A of the controller 60 executes the image processing as an example shown in FIG. 9 by executing the image processing program 61 stored in the ROM 60B. In FIG. 9, a flowchart showing an example of a flow of image processing that is executed in the console 11 of the embodiment is shown.

In Step S100 of FIG. 9, the second acquisition unit 72 acquires the distance image from the distance measurement camera 32. Specifically, the second acquisition unit 72 instructs the distance measurement camera 32 to capture the distance image, and acquires the distance image captured by the distance measurement camera 32 based on the instruction through the I/F unit 64. The distance image acquired by the second acquisition unit 72 is output to the specification unit 74.

In next Step S102, the specification unit 74 acquires the distance to the imaging target based on the distance image. In next Step S104, the specification unit 74 determines whether or not a structure distance image corresponding to the structure of the specific shape described above is detected from the distance image based on the acquired distance. As an example, the specification unit 74 of the embodiment detects a region where a predetermined number or more of pixels representing the same distance in the distance image, and specifically, a predetermined number of pixels having the same pixel value or having a difference between adjacent pixel values equal to or less than a predetermined value continue, as an imaging target distance image corresponding to a certain imaging target. The specification unit 74 detects an image having a predetermined shape as the structure of the specific shape in the detected imaging target distance image, as a structure distance image.

A method of detecting the structure distance image in the distance image is not limited to the method of the embodiment. For example, a distance to the structure of the specific shape or the subject may be obtained as a structure distance in advance from the distance measurement camera 32, and a region of pixels representing a specific structure distance and having a specific shape may be detected as a structure distance image.

In imaging in the form shown in FIG. 1 or the form shown in FIG. 4B, a structure of a specific shape may not be imaged in both the radioscopy apparatus 10 and the distance measurement camera 32. In other words, the structure of the specific shape, such as the wheelchair 50 or the stretcher 51 may not be an imaging target. In such a case, a structure distance image is not detected from the distance image.

In a case where a structure distance image is not detected from the distance image, negative determination is made in Step S104, and the process progresses to Step S106. In a case where a structure distance image is not detected from the distance image, the structure image 47B representing the structure of the specific shape is not included in the radiographic image 45 captured by the radioscopy apparatus 10. Accordingly, in Step S106, the specification unit 74 derives information representing that a structure image is absent, and then, the process progresses to Step S110.

On the other hand, in a case where a structure distance image is detected from the distance image, affirmative determination is made in Step S104, and the process progresses to Step S108. In Step S108, the specification unit 74 derives positional information representing the position of the structure image 47B in the radiographic image 45, and then, the process progresses to Step S110. In this case, the structure image 47B representing the structure of the specific shape is included in the radiographic image 45 captured by the radioscopy apparatus 10. As described above, the distance image and the radiographic image 45 are registered in advance, and thus, the specification unit 74 derives the positional information representing the position of the structure image 47B in the radiographic image 45 from the position of the structure distance image in the distance image.

It is preferable that the processing of each of Steps S100 to S108 described above is executed at any timing before imaging of the radiographic image 45 by the radioscopy apparatus 10, and at least before the console 11 acquires the radiographic image 45 output from the radiation detector 33. Examples of any timing in radioscopy by the radioscopy apparatus 10 include a period during which the operator OP releases the depression of the foot switch 22 and the irradiation of the radiation R from the radiation source 30 is stopped while radioscopy corresponding to the imaging order is performed. Any timing may be a timing synchronized with a timing at which the radiation detector 33 captures a radiographic image for offset correction of the radiographic image 45 in a case where the irradiation of the radiation R is stopped.

In next Step S110, the specification unit 74 determines whether or not the radiographic image 45 is acquired from the radioscopy apparatus 10, and more specifically, from the radiation detector 33. Until the radiographic image 45 is acquired, negative determination is made in Step S110. On the other hand, in a case where the radiographic image 45 is acquired, affirmative determination is made in Step S110, and the process progresses to Step S112.

In Step S112, the specification unit 74 specifies the structure image 47B included in the radiographic image 45. Specifically, in a case where the positional information of the structure image 47B is derived in Step S108 described above, the specification unit 74 specifies the structure image 47B included in the radiographic image 45 based on the positional information. In a case where information representing that the structure image 47B is absent is derived in Step S106 described above, the specification unit 74 specifies that the structure image 47B is not included in the radiographic image 45.

In next Step S114, the specification unit 74 derives the patient image region 49A in the radiographic image 45. As an example, in the embodiment, a correspondence relationship between the irradiation field IF to be adjusted by the collimator 31 of the radioscopy apparatus 10 and a range (size and position) of the radiographic image 45 to be captured with the irradiation field IF is determined in advance. The specification unit 74 derives a greatest range in the range not including the structure image 47B as the patient image region 49A based on the predetermined correspondence relationship. The specification unit 74 outputs information representing the position of the patient image region 49A in the radiographic image 45 to the image processing unit 76.

In next Step S116, the image processing unit 76 executes the image processing including the above-described dynamic range compression processing on the radiographic image. As described above, in a case where the structure image 47B is included in the radiographic image 45, the image processing unit 76 executes the image processing only for the visibility of the patient image region 49A not including the structure image 47B in the radiographic image 45. On the other hand, in a case where the structure image 47B is not included in the radiographic image 45, the image processing unit 76 executes the image processing including the above-described dynamic range compression processing to the entire radiographic image 45.

In next Step S118, the image processing unit 76 outputs the radiographic image 45 subjected to the image processing in Step S116 to the operator monitor 21 of the radioscopy system 2. In next Step S120, the image processing unit 76 determines whether or not to end the image processing. Until a predetermined end condition is satisfied, negative determination is made in Step S120, the process returns to Step S110, and the processing of Steps S110 to S118 is repeated. On the other hand, in a case where the predetermined end condition is satisfied, affirmative determination is made in Step S120. Although the predetermined end condition is, for example, a case where the operator OP releases the depression of the foot switch 22 or a case where the console 11 receives an end instruction of imaging input by the operator OP, the present disclosure is not limited thereto. In a case where the processing of Step S120 ends in this manner, the image processing ends.

In this way, the specification unit 74 of the console 11 of the embodiment specifies the structure image 47B included in the radiographic image 45 based on the distance image captured by the distance measurement camera 32. In a case where the structure image 47B is included in the radiographic image 45, the image processing unit 76 executes the image processing including the dynamic range compression processing only for the visibility of the patient image region 49A not including the structure image 47B. Accordingly, with the console 11 of the embodiment, it is possible to execute the image processing to the patient image 47A and to improve the image quality of the radiographic image 45 regardless of the structure image 47B. The radiographic image 45 with contrast enhanced and image quality improved in this manner is displayed on the operator monitor 21, and thus, it is possible to improve visibility or the like of the operator OP. With the console 11 of the embodiment, it is possible to make the operator OP unconscious of the structure image 47B in the radiographic image 45.

A method of specifying the structure image 47B from the radiographic image 45 is not limited to the above-described method. For example, as described in the following modification examples, the structure image 47B may be specified from the radiographic image 45 using a learned model 63.

Modification Example 1

Figure 10:
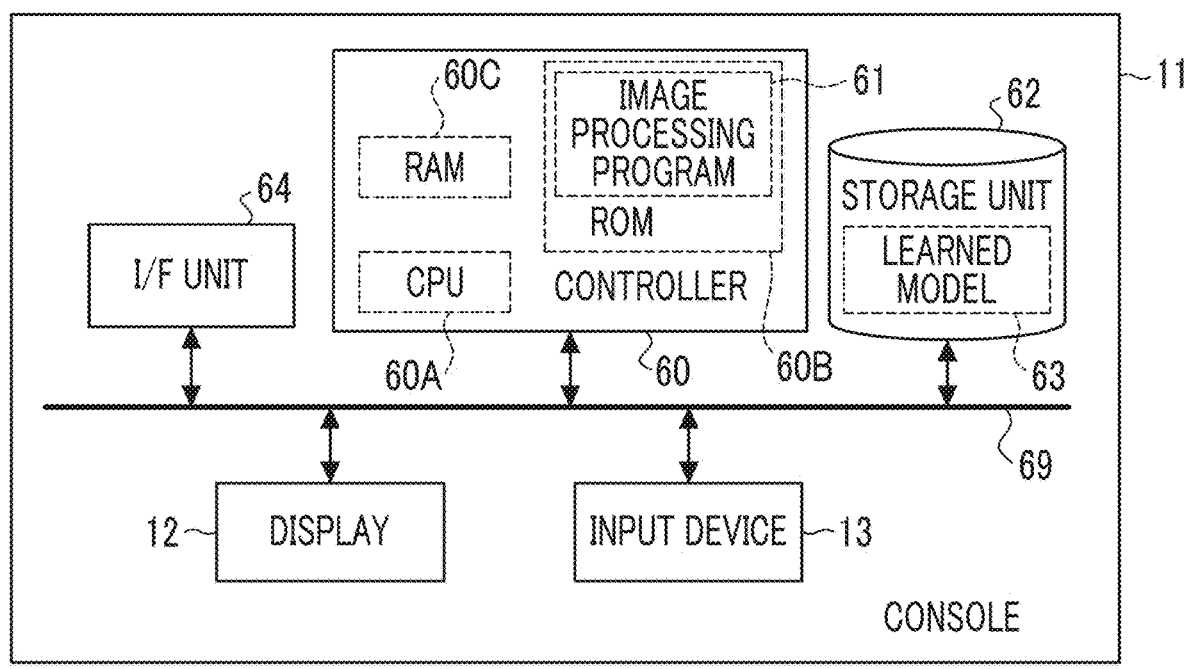
FIG. 10 is a block diagram showing an example of the hardware configuration of a console of a modification example.

FIG. 10 is a block diagram showing an example of the hardware configuration of a console 11 of the modification example. As shown in FIG. 10, in the console 11 of the modification example, the learned model 63 is stored in the storage unit 62.

Figure 11:
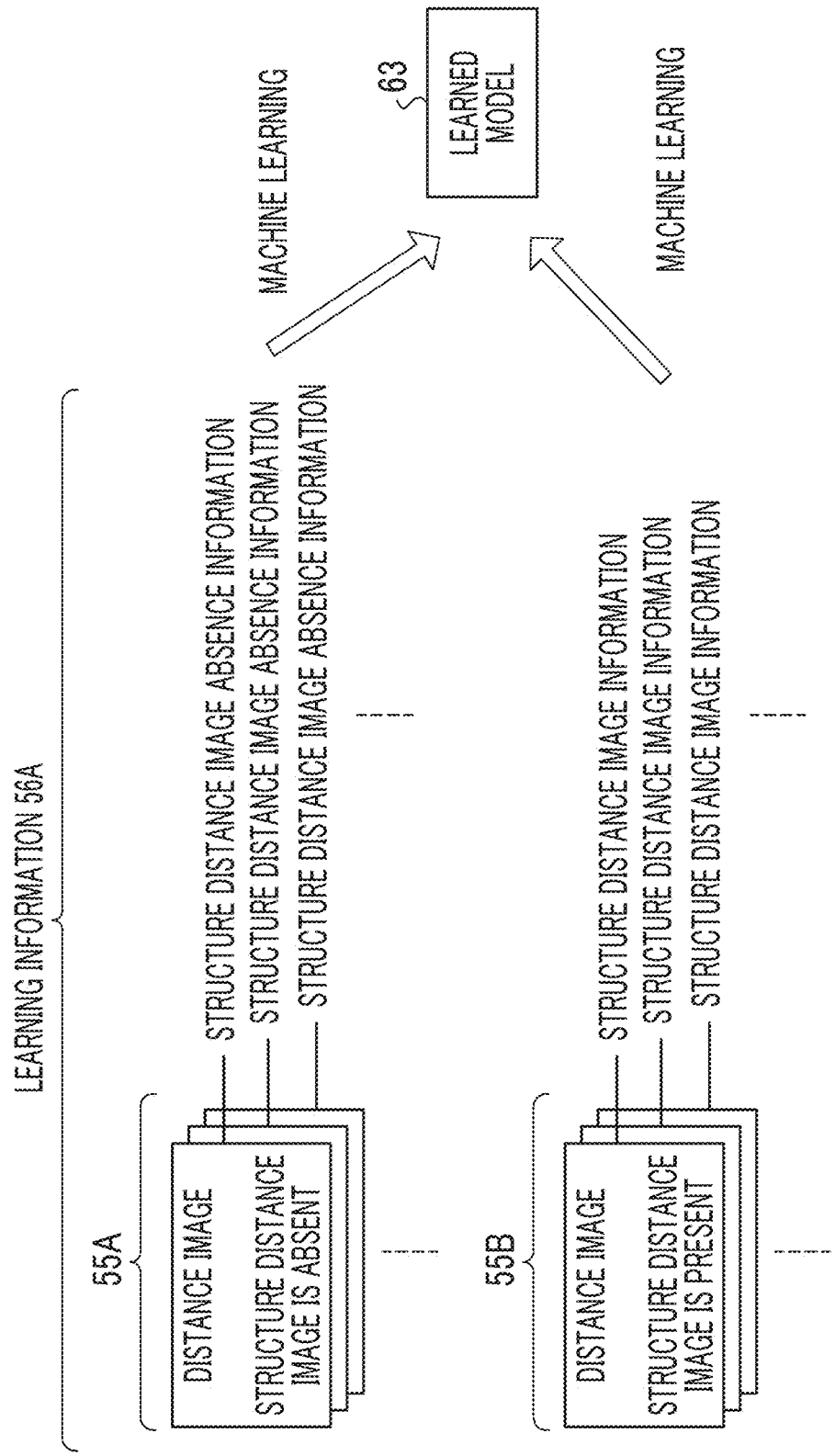
FIG. 11 is a diagram illustrating a learned model of Modification Example 1.
Figure 12:
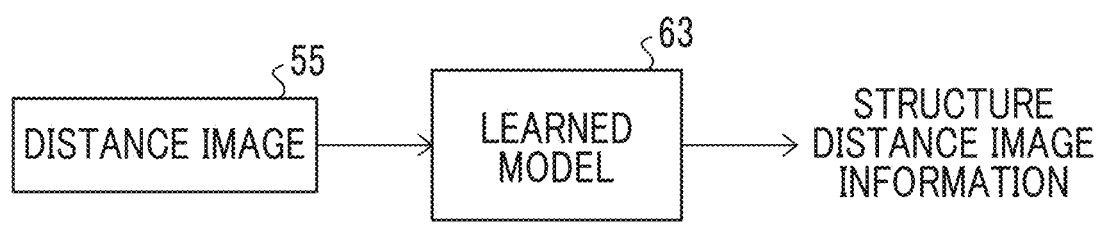
FIG. 12 is a diagram illustrating an input and an output of the learned model of Modification Example 1.

As shown in FIG. 11, the learned model 63 is a model learned in advance using learning information 56A. In the embodiment, as an example, as shown in FIG. 11, the learned model 63 is generated by machine learning using the learning information 56A. As an example, the learning information 56A of the embodiment includes a plurality of distance images 55A in which a structure distance image is not included and structure distance image absence information representing that a structure distance image is not included is associated, and a plurality of distance images 55B in which a structure distance image is included and structure distance image information representing the position of the structure distance image is associated. The learned model 63 is generated from the distance images 55A and the distance images 55B. Examples of the learned model 63 include a neural network model. As an algorithm of learning, for example, a back propagation method can be applied. With the above-described learning, as an example, as shown in FIG. 12, the learned model 63 having the distance image 55 as an input and the structure distance image information representing a detection result of the structure distance image as an output is generated. Examples of the structure distance image information include information representing the presence or absence of a structure distance image and, in a case where a structure distance image is present, information representing the position of the structure distance image in the distance image 55.

In the modification example, the processing of Step S102 of the above-described image processing (see FIG. 9) is not executed, and in Step S104, the specification unit 74 performs determination based on a detection result using the learned model 63.

Modification Example 2

Figure 13:
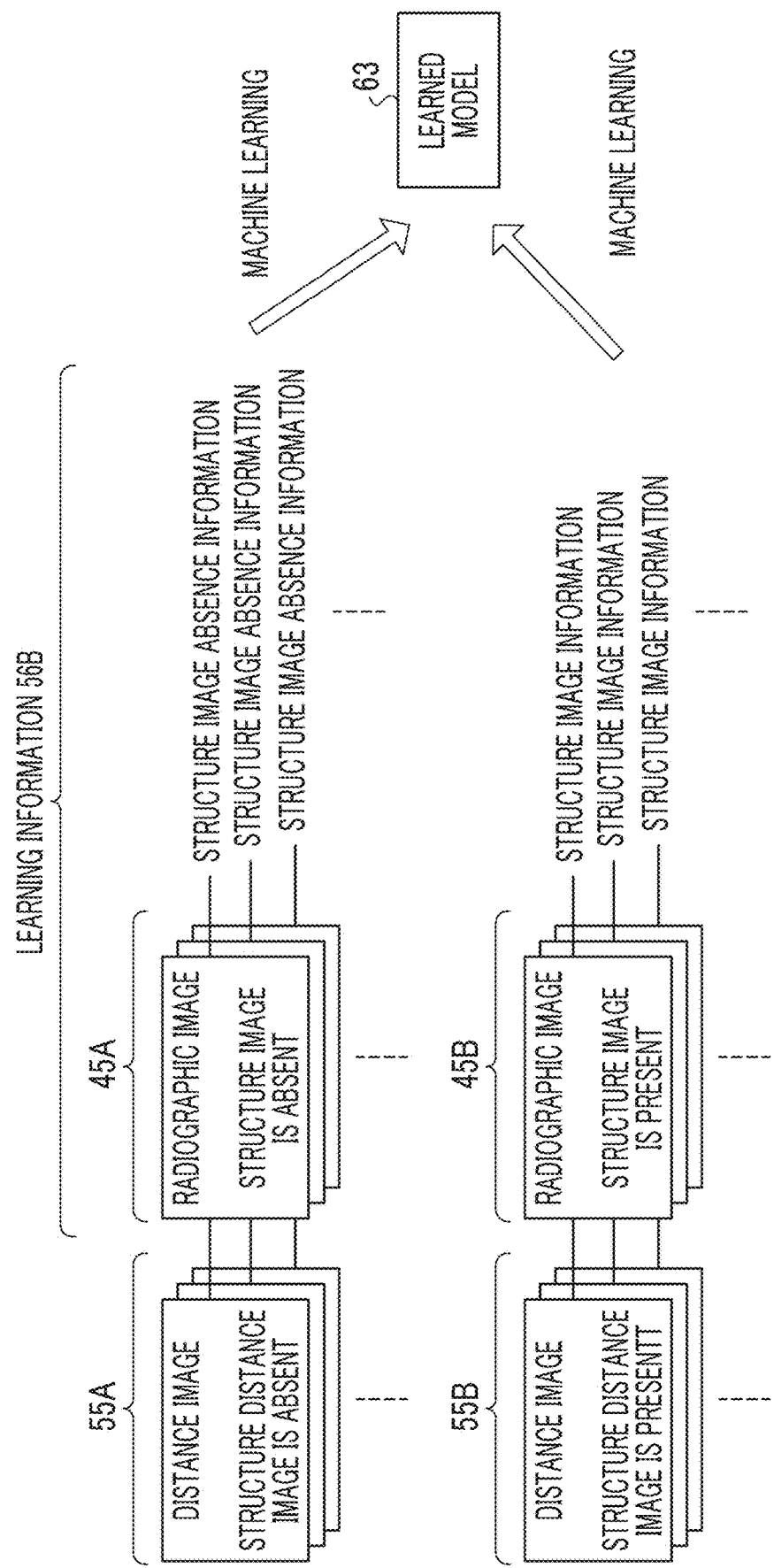
FIG. 13 is a diagram illustrating a learned model of Modification Example 2.

FIG. 13 shows a modification example of the learned model 63. As shown in FIG. 13, the learned model 63 of the modification example is a model learned in advance using learning information 56B. In the embodiment, as an example, as shown in FIG. 13, the learned model 63 is generated by machine learning using the learning information 56B. As an example, the learning information 56B of the embodiment includes combinations of a plurality of distance images 55A in which a structure distance image is not included and a plurality of radiographic images 45A that correspond to the distance images 55A and in which structure image absence information representing that a structure image 47B is not included is associated. The learning information 56B includes combinations of a plurality of distance images 55B in which a structure distance image is included and a plurality of radiographic images 45B that correspond to the distance images 55B and in which structure image information representing the position of the structure image 47B is associated.

Figure 14:
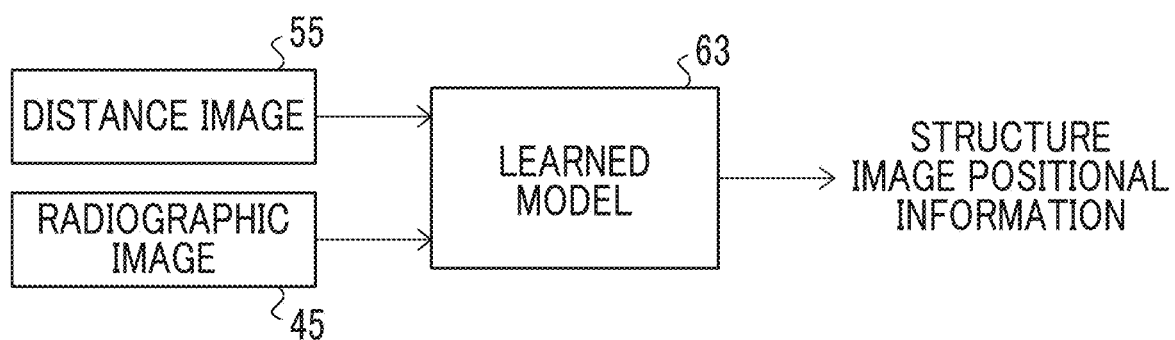
FIG. 14 is a diagram illustrating an input and an output of the learned model of Modification Example 2.

The learned model 63 is generated from the combinations of the distance images 55A and the radiographic images 45A and the combinations of the distance images 55B and the radiographic images 45B. Examples of the learned model 63 include a neural network model as in Modification Example 1. As an algorithm of learning, for example, a back propagation method can be applied. With the above-described learning, as an example, as shown in FIG. 14, the learned model 63 having the radiographic images 45 and the distance images 55 as inputs and structure image positional information representing the position of the structure image 47B in the radiographic image 45 as an output is generated. Examples of the structure image positional information include information representing the presence or absence of the structure image 47B and, in a case where the structure image 47B is present, information representing the position of the structure image 47B in the radiographic image 45.

In the modification example, the processing of Steps S102 to S106 of the above-described image processing (see FIG. 9) is not executed, and in Step S112, the specification unit 74 performs the specification of the structure image 47B using the learned model 63.

In this way, according to Modification Example 1 and Modification Example 2, the learned model 63 is used in the processing of specifying the structure image 47B from the radiographic image 45. For this reason, it is possible to more accurately and easily specify the structure image 47B.

Second Embodiment

In the first embodiment, a form in which the structure image 47B is specified from the radiographic image 45 using the distance image 55 captured by the distance measurement camera 32 has been described. In contrast, in the embodiment, a form in which the structure image 47B is specified from the radiographic image 45 further using a visible light image captured by a visible light camera will be described. In regard to the radioscopy system 2, the radioscopy apparatus 10, and the console 11 of the embodiment, detailed description of the same configuration and operation as in the first embodiment will not be repeated.

Figure 15:
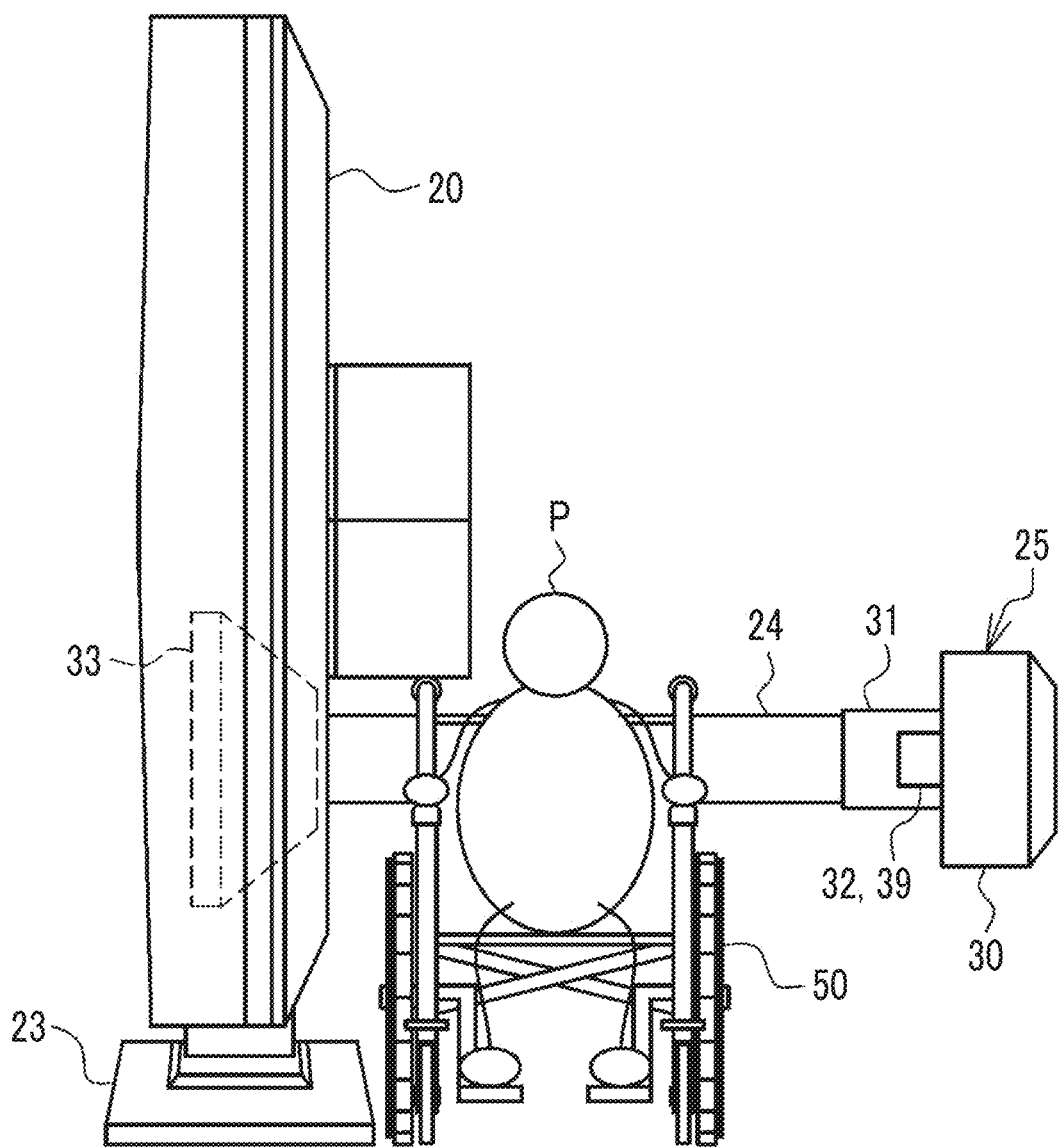
FIG. 15 is a diagram showing an example of a manner in which radioscopy is performed on a patient in a wheelchair with a radioscopy apparatus of a second embodiment with the imaging table and the post in the upright state.

As shown in FIG. 15, the radioscopy system 2 of the embodiment comprises a visible light camera 39 near the distance measurement camera 32 of the radioscopy apparatus 10. The visible light camera 39 is a so-called general camera, and is a camera that captures a visible light image. Specifically, the visible light camera 39 receives visible light reflected by the imaging target with an imaging element (not shown) and captures a visible light image based on the received visible light. The visible light camera 39 of the embodiment is an example of a "visible light image capturing apparatus" of the present disclosure. An imaging range of the visible light camera 39 of the embodiment includes the whole of the imaging region SA of the radioscopy apparatus 10. Accordingly, the visible light camera 39 of the embodiment captures a visible light image of the imaging target of the radioscopy apparatus 10. Imaging of a visible light image is not performed to an imaging target behind (under) another imaging target as viewed from the distance measurement camera 32 among imaging targets in the imaging region SA.

In the embodiment, the distance image 55 captured by the distance measurement camera 32, the visible light image captured by the visible light camera 39, and the radiographic image 45 captured by the radioscopy apparatus 10 are registered in advance. Specifically, correspondence relationship information indicating an image represented by a pixel in the distance image 55 or an image represented by a pixel in the visible light image to which an image represented by a pixel in the radiographic image 45 corresponds is obtained in advance.

Figure 16:
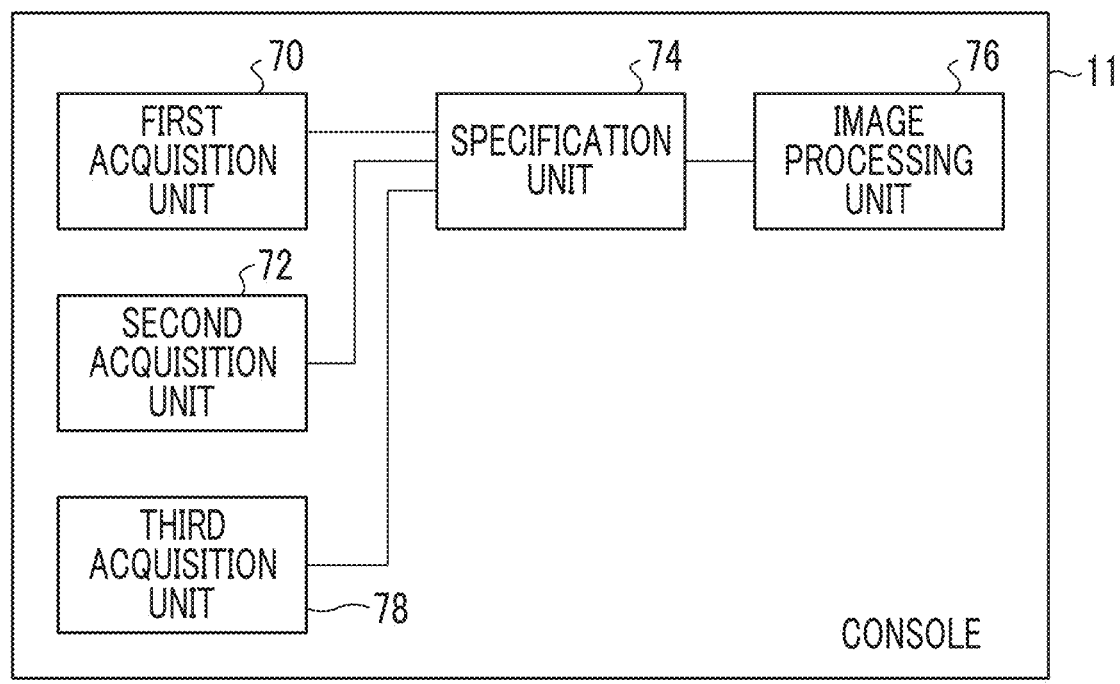
FIG. 16 is a functional block diagram showing an example of the functional configuration of a console of the second embodiment.

FIG. 16 is a functional block diagram of an example of the functional configuration of the console 11 of the embodiment. As shown in FIG. 16, the console 11 of the embodiment is different from the console 11 (see FIG. 6) of the first embodiment in that a third acquisition unit 78 is further provided.

The third acquisition unit 78 has a function of acquiring the visible light image captured by the visible light camera 39. As an example, the third acquisition unit 78 of the embodiment acquires image data representing the visible light image captured by the visible light camera 39 from the visible light camera 39 through the I/F unit 64. Image data representing the visible light image acquired by the third acquisition unit 78 is output to the specification unit 74.

The specification unit 74 of the embodiment specifies the structure image 47B included in the radiographic image 45 based on the distance to the imaging target acquired from the distance image 55 and a shape of the imaging target detected from the visible light image. A method of detecting the shape of the imaging target from the visible light image captured by the visible light camera 39 is not particularly limited. For example, the specific shape of the structure image may be used as a template, and image analysis may be performed to the visible light image using the template, thereby detecting the shape of the imaging target as the structure having the specific shape.

As an example, in the console 11 of the embodiment, the CPU 60A of the controller 60 executes the image processing program 61 stored in the ROM 60B, whereby the CPU 60A functions as the first acquisition unit 70, the second acquisition unit 72, the specification unit 74, the image processing unit 76, and the third acquisition unit 78.

The operation of the console 11 of the embodiment, and specifically, image processing that is executed in the console 11 will be described.

Figure 17:
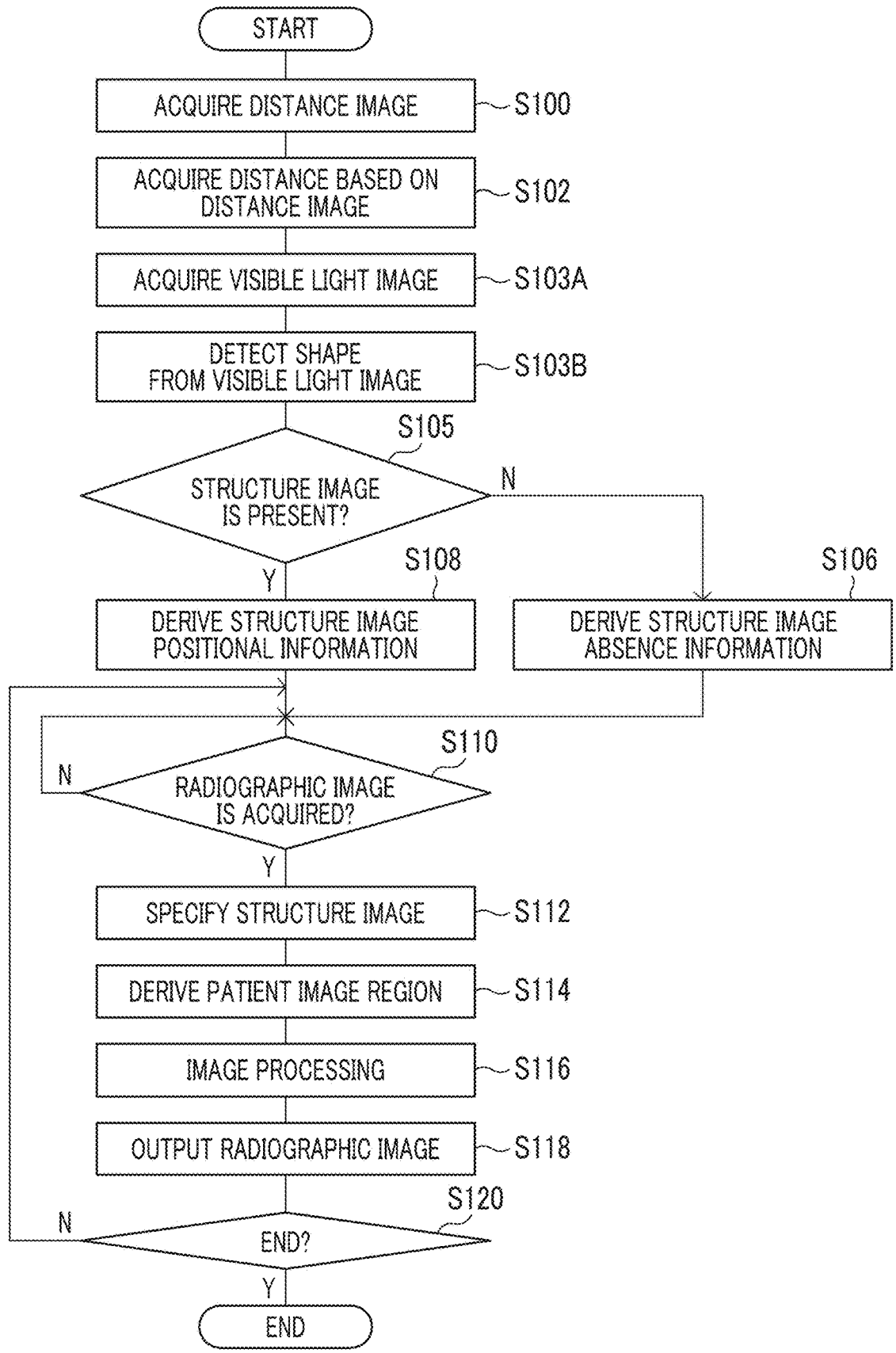
FIG. 17 is a flowchart showing an example of a flow of image processing in the console of the second embodiment.

FIG. 17 is a flowchart showing an example of a flow of image processing that is executed in the console 11 of the embodiment. As shown in FIG. 17, the image processing of the embodiment includes processing of Steps S103A, S103B, and S105, instead of Steps S102 and S104 of the image processing (see FIG. 9) of the first embodiment.

In Step S103A of FIG. 17, as described above, the third acquisition unit 78 acquires the visible light image from the visible light camera 39. Specifically, the third acquisition unit 78 instructs the visible light camera 39 to capture the visible light image and acquires the visible light image captured by the visible light camera 39 based on the instruction through the I/F unit 64. The visible light image acquired by the third acquisition unit 78 is output to the specification unit 74.

In next Step S103B, the specification unit 74 detects the shape of the imaging target based on the visible light image as described above. In next Step S105, the specification unit 74 determines whether or not the structure image 47B is included in the radiographic image 45 based on the acquired distance and the detected shape.

In this way, in the embodiment, the structure having the specific shape is detected based on the visible light image captured by the visible light camera 39, and thus, it is possible to more accurately detect the specific shape.

As described above, the console 11 of each embodiment described above comprises the CPU 60A as at least one processor. The CPU 60A acquires the radiographic image 45 obtained by imaging the imaging region SA where the patient P is present, with the radioscopy apparatus 10 using the radiation R emitted from the radiation source 30 and applied to the irradiation field IF adjusted by the collimator 31. The CPU 60A specifies the structure image 47B that is included in the radiographic image 45 and represents the structure of the specific shape having transmittance of the radiation R lower than the patient P, based on the specific shape. The CPU 60A executes the image processing corresponding to the structure image 47B on the patient image region 49A imaged by the radioscopy apparatus 10 in a case where the irradiation field IF excluding the position of the structure is set as the irradiation field IF, in the region in the radiographic image 45.

In this way, with the console 11 of each embodiment, it is possible to appropriately execute the image processing on the patient image region 49A regardless of the structure image 47B that has low transmittance of the radiation R and is captured with a comparatively lower density than the patient image 47A in the radiographic image 45.

In particular, in radioscopy by the radioscopy apparatus 10, auto brightness control (ABC) may be performed. As known in the art, the ABC is feedback control where, to maintain the brightness of the radiographic image 45 within a given range, during radioscopy, the tube voltage and the tube current given to the radiation tube 40 are finely adjusted based on a brightness value (for example, an average value of brightness values of a center region of the radiographic image 45) of the radiographic image 45 sequentially output from the radiation detector 33. With the ABC, the brightness of the radiographic image 45 is prevented from being extremely changed due to body movement or the like of the patient P or the radiographic image 45 is prevented from being hardly observed. Note that, as described above, in a case where the low density image is included in the radiographic image 45, the contrast of the patient image 47A may decrease. In contrast, in the embodiment, it is possible to suppress the decrease in contrast of the patient image 47A even though the structure image 47B is included.

Accordingly, with the console 11 of each embodiment described above, it is possible to improve the image quality of the radiographic image 45 that is captured by the radioscopy apparatus 10 and is displayed on the operator monitor 21.

With the console 11 of the embodiment, it is possible to specify the structure image 47B included in the radiographic image 45 to be input before imaging of the radiographic image 45, and in particular, before the radiographic image 45 is input to the console 11. Accordingly, it is possible to more quickly execute the image processing to the radiographic image 45. In particular, in radioscopy of the radioscopy apparatus 10, a plurality of radiographic images 45 are continuously captured. An imaging interval of the radiographic images 45 in this case is comparatively short, and for example, imaging is performed at a frame rate of 30 frames per second (fps). Even in such a case, it is possible to execute appropriate image processing with a high real time property from the first radiographic image 45.

In the respective embodiments described above, although a form in which the distance measurement camera 32 is used as an example of a distance image capturing apparatus and captures the distance image using the TOF system has been described, the distance image capturing apparatus that captures the distance image is not limited to the TOF camera. For example, a form may be made in which a distance image capturing apparatus that irradiates an imaging target with patterned infrared light and captures a distance image corresponding to reflected light from the imaging target is used and applies a structured light system to capture the distance image. For example, a form may be made in which a depth from defocus (DFD) system that restores a distance based on a degree of blurriness of an edge region imaged in a distance image is applied. In a case of the form, for example, a form is known in which a distance image captured with a monocular camera using a color aperture filter is used.

In the above-described embodiments, although a form in which detection regarding the specific shape of the structure is performed using only the distance image captured by the distance measurement camera 32 or the distance image and the visible light image captured by the visible light camera 39 has been described, the present disclosure is not limited to the form. For example, detection regarding the specific shape of the structure may be performed using only the visible light image captured by the visible light camera 39. In this case, for example, the second acquisition unit 72 in the second embodiment may not be provided, and detection regarding the specific shape may be performed only from the visible light image.

In the respective embodiments described above, although the radioscopy apparatus 10 is exemplified as the radiography apparatus, the present disclosure is not limited thereto. The radiography apparatus may be an apparatus that can image the radiographic image of the subject, and may be, for example, a radiography apparatus that performs general imaging or a mammography apparatus.

In the respective embodiments described above, although the patient P is exemplified as the subject, the present disclosure is not limited thereto. The subject may be other animals, and may be, for example, a pet, such as a dog or a cat, or a domestic animal, such as a horse or cattle.

In the respective embodiments described above, although a form in which the console 11 is an example of the image processing apparatus of the present disclosure has been described, an apparatus other than the console 11 may have the functions of the image processing apparatus of the present disclosure. In other words, for example, the radioscopy apparatus 10 or an external apparatus other than console 11 may have a part or all of the functions of the first acquisition unit 70, the second acquisition unit 72, the specification unit 74, and the image processing unit 76.

In the embodiment, for example, as the hardware structures of processing units that execute various kinds of processing, such as the first acquisition unit 70, the second acquisition unit 72, the specification unit 74, and the image processing unit 76, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like, in addition to a CPU that is a general-purpose processor executing software (program) to function as various processing units, as described above.

One processing unit may be configured of one of various processors described above or may be configured of a combination of two or more processors (for example, a combination of a plurality of FPGAs or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, as the hardware structure of various processors is, more specifically, an electric circuit (circuitry), in which circuit elements, such as semiconductor elements, are combined can be used.

In the above-described embodiments, although an aspect in which the image processing program 61 is stored (installed) in advance in the storage unit 62 has been described, the present disclosure is not limited thereto. The image processing program 61 may be provided in a form of being recorded in a recording medium, such as a compact disc read only memory (CD-ROM), a digital versatile disc read only memory (DVD-ROM), and a universal serial bus (USB). Alternatively, a form may be made in which the image processing program 61 is downloaded from an external apparatus through a network.

What is claimed is:

1. An image processing apparatus comprising:
at least one processor,
wherein the processor is configured to:
acquire a radiographic image obtained by imaging an imaging region where a subject is present, with a radiography apparatus using radiation emitted from a radiation source and applied to an irradiation field adjusted by a collimator,
specify a structure image that is included in the radiographic image and represents a structure of a specific shape having transmittance of radiation lower than the subject, based on the specific shape,
execute image processing on a region of the radiographic image that excludes a position of the structure,
acquire a distance image captured by a distance image capturing apparatus, the distance image representing a distance to an imaging target that is in the imaging region, and acquire a distance to the imaging target based on the distance image, and
detect, from the distance image and based on the distance, a structure distance image corresponding to the specific shape, and specify the structure image from the radiographic image, based on the distance and the specific shape, the structure image being an image corresponding to the structure distance image,
wherein the processor is configured to detect the structure distance image based on a learned model trained in advance using a plurality of distance images with the structure in the imaging region as the imaging target, and
wherein the image processing is a dynamic range compression processing that is determined and performed according to characteristics of a region other than the structure image in the radiographic image.

2. The image processing apparatus according to claim 1, wherein the distance image capturing apparatus captures the distance image using a time-of-flight (TOF) system.

3. The image processing apparatus according to claim 1, wherein the processor is configured to specify the structure image based on a learned model learned in advance using a plurality of combinations of the radiographic image and the distance image with the structure in the imaging region as the imaging target.

4. The image processing apparatus according to claim 1, wherein the processor is configured to:
acquire a visible light image obtained by imaging the imaging region with a visible light image capturing apparatus, and
specify the structure image included in the radiographic image based on a shape detected from the visible light image and the distance.

5. The image processing apparatus according to claim 1, wherein the processor is configured to:
acquire a visible light image obtained by imaging the imaging region with a visible light image capturing apparatus,
detect a structure visible light image corresponding to the specific shape from the visible light image, and
specify, as the structure image, an image corresponding to the structure visible light image from the radiographic image.

6. The image processing apparatus according to claim 1, wherein the structure consists of metal.

7. The image processing apparatus according to claim 1, wherein the structure is a wheelchair.

8. The image processing apparatus according to claim 1, wherein the structure is a stretcher.

9. The image processing apparatus according to claim 1, wherein the processor is configured to execute the image processing on a region other than the structure image in the radiographic image.

10. The image processing apparatus according to claim 1, wherein the image processing is contrast enhancement processing.

11. A radiography system comprising:
a radiography apparatus that captures a radiographic image of a subject; and
the image processing apparatus according to claim 1.

12. An image processing method, comprising, by a computer:
acquiring a radiographic image obtained by imaging an imaging region where a subject is present, with a radiography apparatus using radiation emitted from a radiation source and applied to an irradiation field adjusted by a collimator,
specifying a structure image that is included in the radiographic image and represents a structure of a specific shape having transmittance of radiation lower than the subject, based on the specific shape, and
executing image processing on a region of the radiographic image that excludes a position of the structure,
acquiring a distance image captured by a distance image capturing apparatus, the distance image representing a distance to an imaging target that is in the imaging region, and acquiring a distance to the imaging target based on the distance image, and
detecting, from the distance image and based on the distance, a structure distance image corresponding to the specific shape, and specifying the structure image from the radiographic image, based on the distance and the specific shape, the structure image being an image corresponding to the structure distance image,
wherein the structure distance image is detected based on a learned model trained in advance using a plurality of distance images with the structure in the imaging region as the imaging target, and
wherein the image processing is a dynamic range compression processing that is determined and performed according to characteristics of a region other than the structure image in the radiographic image.

13. A non-transitory computer-readable storage medium storing an image processing program executable by a computer to perform processing comprising:
acquiring a radiographic image obtained by imaging an imaging region where a subject is present, with a radiography apparatus using radiation emitted from a radiation source and applied to an irradiation field adjusted by a collimator, specifying a structure image that is included in the radiographic image and represents a structure of a specific shape having transmittance of radiation lower than the subject, based on the specific shape, and executing image processing on a region of the radiographic image that excludes a position of the structure, acquiring a distance image captured by a distance image capturing apparatus, the distance image representing a distance to an imaging target that is in the imaging region, and acquiring a distance to the imaging target based on the distance image, and detecting, from the distance image and based on the distance, a structure distance image corresponding to the specific shape, and specifying the structure image from the radiographic image, based on the distance and the specific shape, the structure image being an image corresponding to the structure distance image, wherein the structure distance image is detected based on a learned model trained in advance using a plurality of distance images with the structure in the imaging region as the imaging target, and wherein the image processing is a dynamic range compression processing that is determined and performed according to characteristics of a region other than the structure image in the radiographic image.

14. The image processing apparatus according to claim 1, wherein the image processing processes the image based on at least one of an image characteristic or an image density of the region other than the structure image in the radiographic image.

15. The image processing method according to claim 12, wherein the image processing processes the image based on at least one of an image characteristic or an image density of the region other than the structure image in the radiographic image.

16. The non-transitory computer-readable storage medium according to claim 13, the image processing processes the image based on at least one of an image characteristic or an image density of the region other than the structure image in the radiographic image.

* * * * *